(12) United States Patent
Chilibeck

(10) Patent No.: US 6,946,069 B2
(45) Date of Patent: *Sep. 20, 2005

(54) APPARATUS FOR REMOVING METALLIC PARTICLES FROM EFFLUENT LIQUID WASTE

(75) Inventor: Richard H. Chilibeck, Victoria (CA)

(73) Assignee: SolmeteX, Inc., Northborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/659,597

(22) Filed: Sep. 9, 2003

(65) Prior Publication Data

US 2004/0045882 A1 Mar. 11, 2004

Related U.S. Application Data

(63) Continuation of application No. 09/908,682, filed on Jul. 18, 2001, now Pat. No. 6,692,636, which is a continuation-in-part of application No. 09/768,848, filed on Jan. 23, 2001, now Pat. No. 6,592,754, which is a continuation-in-part of application No. PCT/CA99/00665, filed on Jul. 21, 1999.

(30) Foreign Application Priority Data

Jul. 24, 1998 (CA) .............................................. 2243580

(51) Int. Cl.$^7$ .......................... A61C 17/14; B01D 17/00
(52) U.S. Cl. ......................... 210/97; 210/258; 210/533; 210/539; 433/92
(58) Field of Search ............................ 433/92; 210/539, 210/533, 532.1, 416.1, 258, 112, 406, 97

(56) References Cited

U.S. PATENT DOCUMENTS

| | | | |
|---|---|---|---|
| 691,365 A | * | 1/1902 | Dittler ......................... 210/199 |
| 2,348,167 A | * | 5/1944 | Ransome .................... 210/804 |
| 3,679,053 A | | 7/1972 | Koulovatos et al. |
| 3,862,033 A | | 1/1975 | Rozkydaiek |
| 4,058,897 A | | 11/1977 | Edwards |
| 4,326,952 A | | 4/1982 | Blake |
| 4,328,101 A | | 5/1982 | Broden |
| 4,385,891 A | | 5/1983 | Ligotti |
| 4,710,290 A | | 12/1987 | Briltz |
| 5,017,135 A | | 5/1991 | Meyer |
| 5,613,851 A | * | 3/1997 | Trawoger et al. ............. 433/92 |
| 5,665,245 A | | 9/1997 | Kloss et al. |
| 5,700,378 A | * | 12/1997 | Lee et al. ................... 210/771 |
| 5,770,059 A | | 6/1998 | Rhee |
| 5,797,742 A | | 8/1998 | Fraker |
| 5,885,076 A | | 3/1999 | Ralls et al. |

OTHER PUBLICATIONS

Fraker, The Amalgam Collector, leaflet, Jan. 30, 1998, 5 pages, R & D Services, In., Seattle, USA.

* cited by examiner

Primary Examiner—Terry K. Cecil

(57) ABSTRACT

An apparatus for separating solid particles from the suction effluent of, for example, a dental office, preferably driven by a dental office vacuum pump, includes a surge tank for accommodating effluent overfill connected to a sedimentary deposit tank for sedimentation of effluent particles. A bypass conduit is connected to the surge tank inlet which is equipped with a vacuum break valve for allowing air into the system when the suction openings are closed. The sedimentary deposit tank has a series of baffle chambers through which effluent flows in sequence, and in each of which chambers sediment is deposited for later removal. The surge tank preferably has a liquid level sensor and warning device. Modular filters or adsorbants may be installed in the sedimentary deposit tank, or a modular auxiliary filter may be connected downstream of the tank. Chemical injection may be used to improve sedimentation. A positive air pressure source or auxiliary pumps may be used to drive the effluent, particularly in large installations incorporating multiple surge and deposit tanks. Full tank effluent removal and drying facilities are optionally provided.

14 Claims, 12 Drawing Sheets

APPARATUS FOR REMOVING METALLIC PARTICLES FROM EFFLUENT LIQUID WASTE

RELATED APPLICATION DATA

The present patent application is a continuation of U.S. patent application Ser. No. 09/908,682 filed on 18 Jul. 2001 now U.S. Pat. No. 6,692,636 that is a continuation-in-part of U.S. patent application Ser. No. 09/768,848 filed on 23 Jan. 2001 now U.S. Pat. No. 6,596,754, that is a continuation-in-part of PCT International Patent Application No. PCT/CA99/00665 filed on 21 Jul. 1999 that designates the United States and that claims priority from Canadian patent application No. 2,243,580, filed on 24 Jul. 1998.

FIELD OF THE INVENTION

This invention relates to methods and apparatus suitable to remove particles from effluent waste, and particularly, to remove amalgam and other metallic particles and other abrasive solids from dental office suction effluent.

BACKGROUND OF THE INVENTION

Although amalgams are less frequently used for new dental fillings than was the case some decades ago, nevertheless, amalgams continue to comprise a significant portion of the metallic particle component of dental office effluent because of the fact that old fillings comprising amalgams are drilled out and removed in the effluent waste when new fillings are effected to replace the old. Further, even under current dental practice, an amalgam is preferred for some tooth filling situations. The use of an amalgam in a filling is never a 100% efficient process; amalgam residues are discharged into the dental office effluent. Typically, dental amalgam comprises a number of metals, invariably of course including mercury and almost always at least some silver. Because mercury is a poison that can accumulate in living tissues and can pose a health hazard to species in a food chain exposed to mercury-containing compounds, and since humans are inevitably at the end of the food chain, it follows that effluent containing amalgams can pose a health hazard to the community at large. Also, certain metals such as silver are commercially valuable if recovered in quantity. For those reasons, it is desirable to devise apparatus and processes for removing amalgams from dental office effluent. In addition to removing amalgams, other matter disposed into dental office suction effluent includes aluminum oxides used in air abrasion treatments and other solid waste material. These solid materials tend to wear out or damage vacuum pumps and other equipment downstream of the dental chair suction apparatus, and also constitute effluent water contaminants. Therefore, it is desirable for the apparatus to remove solid abrasive material and other particulate waste from the dental office suction effluent.

Previously known apparatus for removing amalgam particles from dental office suction effluent are known to include a collecting tank for collecting a working day's accumulation of suction effluent from one or more sources of such waste. The waste is sucked from the dental chair suction apparatus and into the collecting tank by a vacuum pump. When the vacuum pump is turned off, an outlet valve is opened and the accumulated waste is deposited into a separation device intended to separate metal particles from the effluent liquid. Flow into the separation device is induced by the head of fluid in the collecting tank. Particles passing through the separation device are separated from the waste by gravity and settle to the bottom of the separation device. The flow rate is dependent on the head inside the collecting tank; as the head diminishes, the flow rate also diminishes. The changes in flow rate are undesirable because the particle separation rate is affected, and the system becomes prone to plugging when the flow rate decreases. Also, since the waste can be deposited only when the vacuum pump is off, waste is usually moved to the separation device at the end of the day. As a result, the collecting tank and separation device tend to be undesirably large.

Another known apparatus is a centrifuge type system that separates heavier metal particles from effluent liquid by collecting the particles at the peripheral wall of the centrifuge. This apparatus does not effectively separate lighter particles, and is expensive to purchase and operate due to the complexity of its mechanical parts.

Yet another known apparatus uses a dedicated mechanical pump to suction waste liquids through a separator device. Again, a dedicated pump can be expensive to purchase and to maintain, and can be undesirably space-consuming.

Such known systems can become quite complex, unwieldy and expensive, as for example that disclosed in Ralls U.S. Pat. No. 5,885,076 granted 23 Mar. 1999. Ralls teaches the use of sedimentation, co-precipitation and filtration in an expensive complicated apparatus that is probably economical, if at all, only for relatively large installations such as a military base dental complex.

An alternative approach described in Ludvigsson U.S. Pat. No. 5,205,743 granted 27 Apr. 1993 involves provision of an air flow in the vicinity of the patient's mouth and suction from that air flow; such apparatus is designed to remove mercury vapour present in the air flow.

The present invention overcomes some of the shortcomings of the prior technology and achieves further advantages that will be apparent after reviewing the following summary of the invention and detailed description.

SUMMARY OF THE INVENTION

According to the invention, an apparatus is provided for removing metal-containing particles and other waste particles from effluent, particularly effluent from a dental office. While herein the term "metal particles" will frequently be employed, it is contemplated that the apparatus is fully capable of separating other solid particles from effluent liquid. Further, with the aid of one or more precipitants, selected solutes may also be removed. In a particular application to be described in detail, effluent from a dental office suction apparatus is discussed; the metal particles are primarily amalgam particles made of mercury and silver alloyed together in an amalgam composition, sometimes with other metals. The metal particles may be in solid particulate form suspended in the liquid, or may be in solute form dissolved in the liquid. The solid particles other than amalgam residues include aluminum oxides used in air abrasion treatment, enamel and dentin from teeth, porcelain, acrylic used in bridges, and prosthetic cementing agents such as zinc phosphate cement used in crowns and bridges. These solid particles are typically suspended in the liquid effluent. Herein such particles are sometimes collectively referred to as "target particles", since they are targeted for removal from the effluent. Such target particles also include precipitated particles obtained in the effluent suspension by precipitation of solutes out of solution.

According to one aspect of the invention, an apparatus for removing metal particles and other solid particles from liquid suction effluent can be installed in a dental office using a pre-existing suction/vacuum pump system to provide fluid flow through the apparatus, without requiring dedicated fluid-flow provenance devices. The apparatus may share a common vacuum pump with conventional dental chair suction apparatus, without interrupting the use of suction equipment at the dental chairs.

Removal of solid particles from liquid suction effluent may be effected by a combination of sedimentation and filtration, assisted by flocculation and precipitation. The invention is not concerned with the specific choice of sedimentary deposit apparatus, a preferred implementation being presented herein as a suitable exemplification of such apparatus. Nor is the invention concerned with specific choices of precipitants, coagulants, flocculants, or other associated materials to effect or facilitate removal of solids or solutes; rather, the invention is concerned with the overall system of solids removal, the provision of apparatus and methods for controlling flow of liquids and gases therein, and the facilitation of removal and replacement of deposit tanks that have been filled with solid waste.

In accordance with a preferred embodiment of the invention, the dental office suction effluent is passed from dental chair suction equipment outlets to a surge tank via a suitable inlet port for the surge tank. The surge tank in turn passes effluent into a sedimentary deposit tank, closed on all sides when in use and preferably readily detachable for emptying and replacement. The sedimentary deposit tank in a preferred embodiment has a series of interior walls that separate the interior of the sedimentary deposit tank into a consecutive series of baffle chambers, including an inlet baffle chamber at the beginning of the series and an outlet baffle chamber at the end of the series. The inlet baffle chamber receives effluent through an inlet port, situated in the preferred embodiment in the lid of the sedimentary deposit tank. The baffle chambers in between the inlet and outlet baffle chambers each in turn receive effluent passed to such chamber by the preceding such baffle chamber in the series. So, liquid effluent flows from the inlet baffle chamber through the interconnected series of baffle chambers to the outlet baffle chamber from whence it passes via a deposit tank outlet port, and preferably thence to an auxiliary filtration unit, as will be further described below.

In such preferred sedimentary deposit tank, each baffle chamber, or at least some of them, receive removable baffles composed of inverse V-shaped strips, inclined either in one dimension, resembling a chevron, or in two dimensions, resembling a gable in appearance. Such baffles are arranged and joined to form channels bounded above and below by the baffle or sedimentary tank surfaces and the side walls of which are formed by the interior divider walls of the baffle chamber into which each baffle is individually inserted. Further, the transverse width of each baffle must be less than the transverse width of the sedimentary deposit tank such that after the insertion and centering of the baffle inside the corresponding baffle chamber, there are apertures between the side walls of the sedimentary tank and the edges of the baffles to allow for the effluent to access and exit the channels formed by the baffles and baffle chamber walls.

In a preferred embodiment of the invention designed to minimize manufacturing costs, the baffles in the baffle chambers are individually formed, configured and dimensioned so that they can be vertically stacked on top of each other or aligned end to end within the baffle compartment. In another preferred embodiment of the invention designed to minimize the costs of assembling sedimentary tank equipment, several vertically spaced baffles are integrally formed as a unit, the configuration and dimensions of such integral baffle units and the baffle compartments selected so that just one integral baffle unit fits into each compartment. Such chevron or gable-shaped baffles or multi-surface integral baffle units can be cheaply and easily manufactured in quantity and simply inserted into a mating baffle compartment without requiring any fasteners, and removed just as easily for cleaning or replacement. In a further embodiment of the invention that provides for additional effluent flow paths through an individual baffle chamber thus promoting efficient sedimentation, two sets of inclined baffle surfaces, each of approximately half the width of an individual baffle chamber, may be fixedly attached on opposite sides of a vertical dividing wall to provide a single unit that can be removably inserted into a compartment of the sedimentary deposit tank. Alternatively, in the interest of modular design, baffle surfaces may be fixedly attached to the baffle chamber walls, such walls being designed to be easily removable from the sedimentary deposit tank for cleaning or replacement of the fixedly attached baffle surfaces.

Each transverse baffle chamber wall of the preferred sedimentary deposit tank separating each baffle chamber from its neighbouring chamber or chambers, extends from the floor of the chamber to a top edge of the chamber and has a notch on its top edge. The bottom edge of each notch is positioned on a pass-over height that is common to all of the chambers. As described above, the water successively enters, passes through the baffle channel and exits each baffle chamber; accordingly, for the baffle chamber to be functional, the horizontal position of the openings (comprising notches and inlet and outlet ports) in each two neighboring chambers must alter in transverse position, so the fluid can enter each chamber on one side, pass through the channel formed by the baffle and exit the chamber on the other end. Because all the notches in one sedimentary deposit tank are preferably at the same vertical level, the second baffle chamber (the neighbour to the inlet baffle chamber immediately downstream thereof) can receive liquid only when the inlet baffle chamber is full and liquid passes over the notch on the intervening transverse baffle chamber wall once it has reached the pass-over height. Similarly, liquid can pass from the second baffle chamber to the third only after the second baffle chamber is full and liquid passes over the notch on top of the wall of the second chamber at the pass-over height to enter the third baffle chamber, and so forth up to the final outlet baffle chamber. When the outlet chamber becomes full, it passes liquid out of the sedimentary deposit tank via the outlet port. In a preferred embodiment of the present invention, the baffle chamber walls are integrally formed as a fixed part of the sedimentary tank structure. Alternatively, however, the baffle chamber walls may be separately formed and removably configured to engage slots in the walls and floor of the sedimentary deposit tank, the slots holding such baffle chamber walls in place inside the sedimentary deposit tank. Optionally, inclined baffle surfaces may be fixedly attached to such removable baffle chamber walls, as mentioned above.

In each baffle chamber, the target particles, being on the average heavier than the liquid effluent, will tend to sink to the bottom of the baffle chamber. Those target particles that are not collected in the first baffle chamber have a chance to be collected in the second, and so on in sequence to the final outlet baffle chamber, so that overall there is a good chance that at least the heavier target particles will be collected at the bottom of the various baffle chambers. Further particle separation can be effected by passing the suction effluent through a plurality of screens or filters positioned in some of the baffle chambers. In a preferred embodiment of the invention, such screens or filters may be located in the final (downstream) baffle chamber or final few baffle chambers to remove particles remaining in the effluent after sedimentation in upstream baffle chambers has taken place before effluent exits the sedimentary deposit tank. Removal of dissolved solute metal particles from the effluent liquid can be achieved by adding a suitable chemical agent such as a precipitant, chelating agent or coagulant, or some combination thereof to the effluent being processed in the sedimentary deposit tank, such chemical agent(s) being selected for combination with solute mercury or silver or both, it being an important objective to remove solute mercury particles, and an objective also to remove solute silver particles from the effluent. The chemical agent precipitates out of the solution metal particles that are in solute form and may facilitate formation of larger particles from smaller particles. Among suitable such agents are precipitants such as potassium iodide (KI), potassium iodate ($KIO_3$), sodium sulfide ($Na_2S$) and various other sulfur compounds; a preferred chelating agent is sodium ethylenediaminetetraacetic acid (sodium EDTA).

The chemical agent(s) may conveniently be injected into the effluent being processed in the sedimentary deposit tank by means of one or more inlet ports preferably located at or near the top of the second or third baffle chamber so that after the largest particles have settled out of solution in the first or second baffle chambers, the chemical agent(s) may act on the entirety of the liquid passing through the remaining downstream baffle chambers in sequence.

If desired, a time-dependent delivery apparatus may provide a metered amount of chemical agent via one or more inlet ports to the second or third baffle chamber, or the chemical agent(s) may be added on a flow-rate-dependent basis, as preferred. The amount of agent added per unit of time or per unit of effluent flow will be dependent in part upon the chemical characteristics of the agent(s) employed, and in part upon the expected concentration of particles in the effluent liquid, and is usually best determined empirically. Accordingly, the amount of chemical agent added to the settlement tank baffle chamber per unit of time or per unit of effluent passing through the baffle chamber is preferably adjustable. According to one aspect of the invention, the introduction of such chemical agent(s) is automatically regulated to occur only when the dental office suction apparatus is operating actively; an overnight shutdown will occur without intervention.

As an alternative to or in combination with the addition of chemical agents such as precipitants, flocculants and chelating agents to the effluent, an adsorbent compound may be used to remove metal ions from solution by surficial adsorption. Such a compound may be incorporated in the construction of the interior of the system settlement tank whereby metal ions dissolved in the effluent passing through the tank are adsorbed by the adsorbent material. A preferred adsorbent material is bentonitic clay. In a preferred embodiment of the present invention, finely divided bentonite clay particles are combined with activated silica particles and enclosed in a porous and permeable membrane, similar in function and appearance to a tea bag. Such bentonite and silica filled membrane may preferably be located in the final few baffle chambers of the sedimentary deposit tank whereby dissolved mercury and other metal ions may be adsorbed by the bentonite, and organic compounds may be adsorbed by the silica prior to the effluent exiting the tank through the tank exit port.

In order to control the growth of bacteria, yeasts, molds, fungi and viruses in the effluent treatment system, a disinfectant is added to the effluent at the individual operatory suction openings. In the preferred embodiment of the invention, the disinfectant is chlorine, bromine or peroxide based, and utilized in a solid dissolvable form.

The flow rate at which the effluent passes through the individual baffle chambers in the sedimentary deposit tank is an important feature of the solid removal system. Precisely, it is desirable to have as slow a flow rate of effluent as possible, to maximize the time for the particles to separate from the effluent in the sedimentary deposit tank. The flow rate of effluent through the sedimentary deposit tank is preferably maintained at a relatively constant value and may be regulated to this end. However, the flow rate may be changed if, for example, the surge tank becomes backed up with effluent. A typical dental office disposes of about one liter of suction effluent per chair per working day, but this quantity may be higher if a cuspidor drain is also connected to the suction apparatus (which may be desirable in the interest of preventing additional undesirable mercury-containing particles from entering the ecosystem, although it is undesirable in that it will typically require a larger-sized separation apparatus to handle the larger volume of effluent). The optimal flow rate setting can be estimated empirically as being equal to the total volume of effluent generated during a duty cycle (for example an 8 hour working day), divided by the total available time for operating the sedimentation system per duty cycle, the resulting rate multiplied by an appropriate safety factor (greater than 1.0) to guard against backup of the system to give the optimal flow rate. For this purpose, the elements of the apparatus according to the invention are suitably selected for dimensions, capacity, vacuum level, etc. (this may be done empirically). In particular, the conduit connected to the sedimentary deposit tank outlet may be sized so as to constrict the flow of liquid effluent. As well, the conduit between the surge tank effluent outlet and the sedimentary deposit tank inlet may be sized so as to constrict the flow of liquid effluent. As well, a throttle valve or other suitable flow regulator such as a needle valve may be installed to control the rate of outflow from the sedimentary deposit tank. A flow meter may also be included to measure the flow rate of effluent exiting the sedimentary deposit tank and display the flow rate measured, permitting the operator to adjust the flow by adjustment of the throttle valve. While alternative automatic or semi-automatic feedback control of the flow can be devised, it would be expected to add appreciably to the cost of manufacture of the equipment.

Although the sedimentary deposit process is effective to remove a satisfactorily high proportion of the target particles desired to be removed from the effluent, the sedimentary deposit tank desirably includes an outlet screen filter in the final baffle chamber to catch any floating materials as well as any other materials that did not settle out in the upstream baffle chambers. Downstream of the sedimentary deposit tank, an auxiliary filtration unit to filter out finer solids may be provided, and a mercury vapour filter may be provided in the air bypass conduit. In the preferred embodiment of the invention, the auxiliary filtration unit is incorporated into the construction of the sedimentary deposit tank and may be located in the final baffle chamber of the tank.

Desirably, at least the sedimentary deposit tank and optionally various filtration units may be connected to the system as removable modular units, or if the filtration unit is desired to be removed independently of the sedimentary deposit tank, each of the sedimentary deposit tank and filtration unit may be devised as removable modular units. For heavier volume effluent processing, two or more sedimentary deposit tanks may be coupled into the system in parallel or in series. It is expected that modular design will be most efficacious for dental offices because it is not to be expected that dentists or their staff will be effectively able to remove deposited sediment from the sedimentary deposit tank nor remove accumulated particle residues from the filtration unit. It is desirable that such removal be done by a competent effluent residue processing facility. Therefore, it is expected to be preferred that the modular sedimentary deposit tank and/or filtration unit be removed periodically and replaced by fresh such tanks or units from time to time as required. The spent tank or unit with an accumulation of metallic particles can then be sent to a processing facility for removal of the metallic particles, possibly chemical separation of mercury from silver, etc., and cleaning of the modular units for re-use. However, if, in any particular installation, it is desired instead that onsite removal of particles be effected, then suitable bypass valves should be provided at the appropriate fluid flow ports, and means provided for removal of particles (e.g. for the sedimentary deposit tank, the entire top wall might be opened or removed, and for the filtration chamber, an access door provided to permit replacement of filters and removal of particles, etc., according to the designer's preference).

Further, according to another aspect of the invention, a full sedimentation tank may be disconnected from active use, and connected to a suction attachment to transfer excess waste water from the sedimentation tank into the surge tank which waste water in turn is retreated in the replacement sedimentation tank. The full tank may then be coupled into a drying conduit connection for a period of time and exposed to tank-drying airflow to permit liquid in the tank to vaporize and be removed in the air outflow. A dry tank is easier to handle by waste processing service personnel than a tank containing a large volume of liquid. Further yet, monitoring means may be provided to determine when the solids content of a sedimentary deposit tank has reached a predetermined level, so as to facilitate transfer of the effluent to a previously idle sedimentary deposit tank.

For the apparatus to work to best advantage without dependence on gravity, a pressure differential must be maintained between the inlet port of the surge tank and the outlet port of either the filtration unit or the outlet port of the sedimentary deposit tank if no filtration unit is present. To this end, the air pressure at the system outlet is maintained at a level less than the air pressure at the system inlet. Assuming that the system operates by using a vacuum pump, the pressures in question are below atmospheric pressure. The system requires that air enter the inlet either via the dental chair suction devices or via a separate air inlet, preferably a vacuum break valve as described below. Consequently, in a vacuum system, the inlet pressure is nearer (but below) atmospheric pressure, while the downstream pressure at the separator outlet is nearer the pressure drawn by the vacuum pump. This pressure differential causes an overall flow of effluent fluid through the surge tank, into the sedimentary deposit tank, thence to the auxiliary filtration unit (if present), to exhaust via the separation system outlet into the vacuum pump exhaust line.

A vacuum pump may apply a partial vacuum at the system inlet port, while at the system outlet port, the vacuum pump draws a higher vacuum, so that there is a pressure differential sufficient to drive effluent liquid properly through the separator system. A pressure differential of the order of 3–10 kPa between inlet and outlet vacuum levels is sufficient to cause liquid effluent to flow through a small simple system, but depending upon the pressure drops within the system, the size of ports, passages, chambers, viscosity of the effluent, etc., the pressure differential may have to be higher. It is best, again, to take an empirical approach and permit the pressure differential to be adjusted manually to suit the user's requirements.

In order to maintain constant air flow through the apparatus when the vacuum pump is operating, there is a spring-loaded vacuum break valve that opens when the suction apparatus openings from the dental chairs are all closed. (Depending upon the spring force exerted on the vacuum break valve, the valve will remain closed when the suction equipment of one or more dental chairs operates, and the requisite input air to the system will be provided via the dental chair suction apparatus.) When the vacuum break valve is opened, the top of the surge tank is open to the ambient air, and suction through the apparatus is effected, causing fluid to flow through the apparatus.

The required air pressure differential between inlet and outlet can instead be positively applied by an air pressure source, but in that event, some means must be interposed at the surge tank to prevent air pressure from driving effluent upstream. According to an aspect of the invention, an additional regulator valve for the surge tank may be provided to accommodate a positive air pressure. The positive air pressure is applied during intervals between successive active operation of the suction drainage system from dental chairs. As dental offices invariably have a source of air under pressure, this source may be used to provide a positive air pressure differential.

If the surge tank becomes full, overflow effluent is sucked through the air outlet port and discharged into the air bypass conduit, thence to the vacuum pump draw line and thence eventually into the municipal drain. However, it is desirable that the system should operate in such a manner as to avoid having the surge tank become completely full, since effluent exiting through the air outlet port will contain particles that will not be separated by the separator. Even if a pinnacle filter or the like catches some of thes particles, solutes and some finer solid particles would be expected eventually to be discharged into the municipal drain. A user of the separator accordingly may wish to adjust the pressure differential of the vacuum system or the size of a constriction in the outlet conduit for the separator, or otherwise suitably adjust the flow rate through the system to prevent overflow. The users may also temporarily suspend discharge of large quantities of liquid into the dental chair suction apparatus if the surge tank is on the verge of becoming full.

It is accordingly preferable that one or more liquid level sensors for sensing liquid level within the surge tank are provided that will cause suitable warning signals to be displayed or heard as the liquid level in the surge tank increases. For example, the sensing mechanism could sense when the surge tank is ¼ full, ½ full, ¾ full, and ⅞ full, and at each threshold liquid level within the surge tank, could provide a suitable warning signal (perhaps using lamps of different colours to correspond to different threshold levels, etc.). Further, when the liquid level in the surge tank has reached (say) the ⅞ level, it may be desirable to alert the users of the system by a more urgent signal (e.g. an audible signal) so that the users will be more urgently warned of the risk that the surge tank may soon be full.

It is also desirable to monitor solids levels in the sedimentary deposit tank or tanks. Solids should preferably accumulate in such tanks only to a fraction of the total tank volume so as not to interfere unacceptably with the settlement process within baffle chambers. As baffle chambers fill up with solids, liquid flow through the tank become impeded or deflected and the tank becomes increasingly less effective to promote settling out of solids. In this specification, reference to a "full" sedimentary deposit tank that should be removed and replaced by a fresh tank, or cleaned out, implies a tank filled with solids to the extent that the user of the system or its designer considers to be acceptable, but does not imply a tank totally filled with solid waste.

Monitoring of solids level within the sedimentary deposit tank may be conveniently be accomplished by a sensor responsive to variations in dielectric constant installed at an appropriate location on an exterior wall of the settlement tank—atop the lid or at the bottom of the sedimentary deposit tank, or preferably at a threshold level position along a side wall. Similar such dielectric-constant variable capacitance-type sensors are commonly used as stud finders for locating studs in closed walls. The location of the sensor on an exterior side wall of the settling tank, so that the sensor path is generally horizontal, may be more reliable in that the distinction between liquid and solids in the path of the sensor is more pronounced than the gradual change in dielectric constant that would be sensed by a sensor atop the tank lid whose sensor path is vertical. In either case, the operating principle is the same—while the solids level in the tank is below the threshold level established for warning detection by the dielectric sensor, no warning signal is supplied, but when the solids level rises to the threshold level above which the sensor provides a warning signal in response to the change in dielectric constant of the solids in the detection path of the sensor, a suitable alert signal (audible, visual, or both as required) can then warn the user that the tank is adequately full and should be removed and replaced, or cleaned.

Monitoring of flow activity within the sedimentary deposit tank may be conveniently be accomplished by a sensor responsive to changes in dielectric constant between effluent liquid and air installed at the top of the tank. When the dental office is working actively, the sedimentary deposit tank quickly fills up and liquid rises to at least some extent in the surge tank. When the office shuts down for the day, effluent drains out of the top of the tank to the extent permitted by the outflow conduit, leaving at least some empty space at the top of the tank. If the dielectric liquid level sensor is installed in that space, the sensor will be responsive to the change in dielectric constant detected when the liquid level in the tank falls below the sensor location. A chemical agent supply pump can be controlled by a suitable control circuit which is responsive to the dielectric liquid level sensor accordingly supply precipitant or other chemical agents at a constant rate determined by the pump to the tank when it is operating, but to shut off when the liquid level in the tank falls below the sensor location. This of course may happen during slack times as well as overnight and on weekends, etc.

The particular sensing devices chosen for sensing liquid level within the surge tank, the warning signal devices and the electrical means for actuating them can all be of conventional design and are not individually per se part of the present invention.

While the invention using a vacuum system is operable if its vacuum source or other source of pressure differential is not connected to the vacuum source for the dental chair suction apparatus, it is convenient and considerably less costly to use a single vacuum pump to serve both the dental chair suction apparatus and the separator apparatus. While, as mentioned, positive air pressure may be used instead of an air pressure differential maintained by vacuum, the system may be somewhat less complex and less expensive to manufacture if a vacuum system is used throughout, utilizing the vacuum pump already present in the dental office.

In a further embodiment of the invention oriented towards large-scale institutional applications in which many dental chairs or other sources of effluent are connected to the same suction and drain services, several parallel-connected sedimentary deposit tanks and associated apparatus, each such composite apparatus including a surge tank and preferably one, or alternatively two attached sedimentary deposit tanks, may be operated in parallel to provide sufficient treatment capacity for large effluent volumes. In such large installations, fluid flow through the individual sedimentary deposit tanks may be controlled by the flow gauge and needle valve means disclosed above, or may preferably be controlled by one or more separate auxiliary effluent vacuum pumps in order to reduce the complexity of adjusting multiple needle valves (or similar individually adjustable flow control devices for each tank) to equalize effluent flow through multiple deposit tanks.

While the invention has been described in the context of a dental office and is expected that dentists will be the primary users of the invention, the invention has application to other similar effluent separation situations. For example, with suitable changes to meet particular situations, the invention may be adapted for use with jewellers' effluent, diamond cutting effluent, dental laboratories effluent, and the like. Where the effluent contains potentially valuable recoverable solids, filters and other removal apparatus and procedures should be selected to maximize the recovery. Equally, for pollution control, recovery of environmental contaminants may be desirable.

DETAILED DESCRIPTION WITH REFERENCE TO THE DRAWINGS

Figure 1:
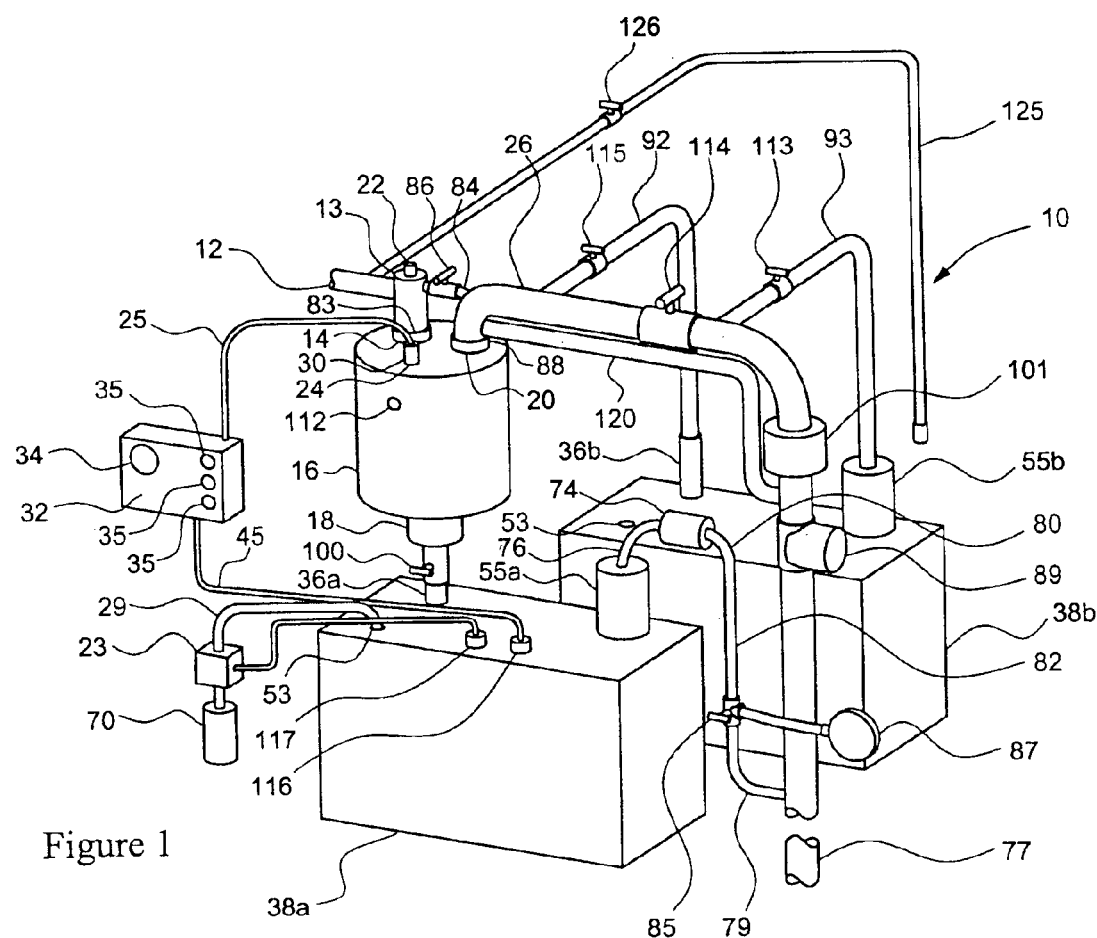
FIG. 1 is a schematic isometric view of a preferred embodiment of particle removal apparatus according to the invention, for particular use in a dental office.
Figure 6:
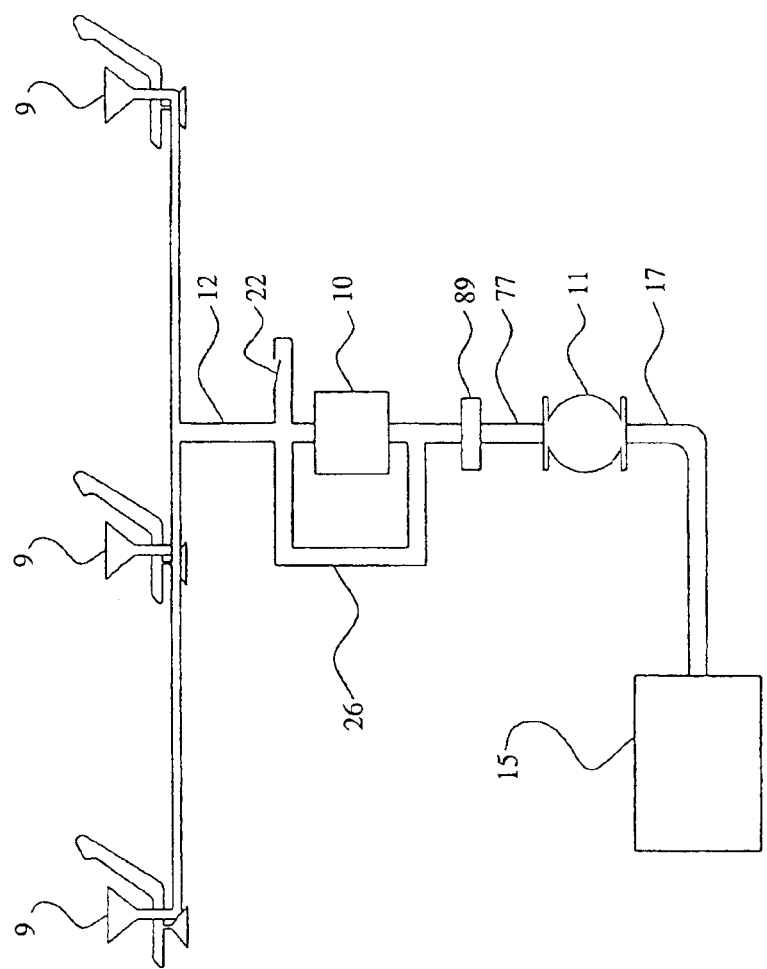
FIG. 6 is a schematic diagram of a dental office vacuum line comprising dental chair suction apparatus openings, the apparatus according to the invention, a vacuum pump and drain.

Separator apparatus 10 according to the preferred embodiment of the invention is shown generally in FIG. 1. The positioning of apparatus 10 in combination with the conduits of conventional suction apparatus in a representative dental office is illustrated in FIG. 6; for greater clarity in the latter figure, bypass conduit 26 and pressure balancing valve (vacuum break valve or air check valve) 22, both of which will be further described below, are specifically schematically shown. The separator apparatus 10 is installed downstream of at least one suction apparatus opening 9 (sometimes referred to herein as an "operatory") associated with a dental chair, and upstream of a vacuum pump 11. The suction apparatus opening 9, apparatus 10, and vacuum pump 11 are interconnected to form a vacuum line in which there is a continuous conduit for fluid to flow from each suction apparatus opening 9 to the vacuum pump 11. When operating, the vacuum pump 11 creates a pressure differential along the vacuum draw line 77 that is coupled to all vacuum lines upstream, thereby generating a suction force along a path from the vacuum pump 11 through the apparatus 10 and to each suction apparatus opening 9.

Such effluent from the dental chairs and a quantity of air are sucked through a suction apparatus exhaust conduit 12, through a surge tank inlet pipestem 13 (FIG. 1), and thence into a surge tank inlet port 14 of a surge tank 16. The air inflow required to maintain suction is maintained either via the dental chair suction outlets 9, or if no dental chair suction line is operating, via vacuum break valve 22 atop pipestem 13, as will be described further below.

The mostly liquid effluent normally passes out of the surge tank 16 via surge tank effluent outlet basin 18, while an air outlet port 20 passes effluent air downstream via bypass conduit 26. An optional deflector (not shown) may be positioned at the top of and inside the surge tank 16, between the surge tank inlet port 14 and the air outlet port 20, and would extend downward within surge tank 16 to a selected depth, serving as a baffle to reduce the amount of liquid effluent that is sucked into the air outlet port 20.

The surge tank effluent outlet port 18 passes effluent out of the surge tank 16 and into sedimentary deposit tank 38a and thence into further downstream portions of the apparatus 10 for target particle separation and effluent discharge. A manually operated shut-off valve 100 closes the surge tank outlet basin 18 when the tank 38a is to be removed for cleaning or replacement. When the vacuum pump 11 is operating, the air pressure differential between the surge tank inlet port 14 and downstream outlet conduit 77 leading into vacuum pump 11 (see FIG. 6), forces effluent, and some air, out of the surge tank 16 and into the sedimentary deposit tank 38.

A vacuum at the air outlet port 20 is generated when the vacuum pump 11 is operating, thereby sucking air out of the surge tank 16, to be discharged from the apparatus 10 via common outlet conduit 77 into which bypass line 26 feeds. Matter sucked by the vacuum pump 11, generally free of removed solids as will be described further below, is discharged via vacuum pump exhaust line 17 into a municipal drain of the public sewage system 15. Such effluent matter typically includes amalgam particles and solutes, aluminum oxides used in air abrasion treatment, enamel and dentine from teeth, porcelain, acrylic used in bridges, prosthetic cementing agents such as zinc phosphate cement used in crowns and bridges, and other solid material.

Typically, a pressure differential of the order of 3–10 kPa between the inlet and outlet of the apparatus 10 is sufficient to cause liquid effluent to flow through the system if it is relatively small. However, the pressure differential may have to be higher depending upon the pressure drops within the system, the size of ports, passages, chambers, etc. and the number of dental chairs served. Preferably, an empirical calculation is made and the pressure differential is adjusted manually to suit the user's requirements, although an automatic feedback system could be provided, if desired, to maintain output flow rate within a selected range of values.

Figure 2:
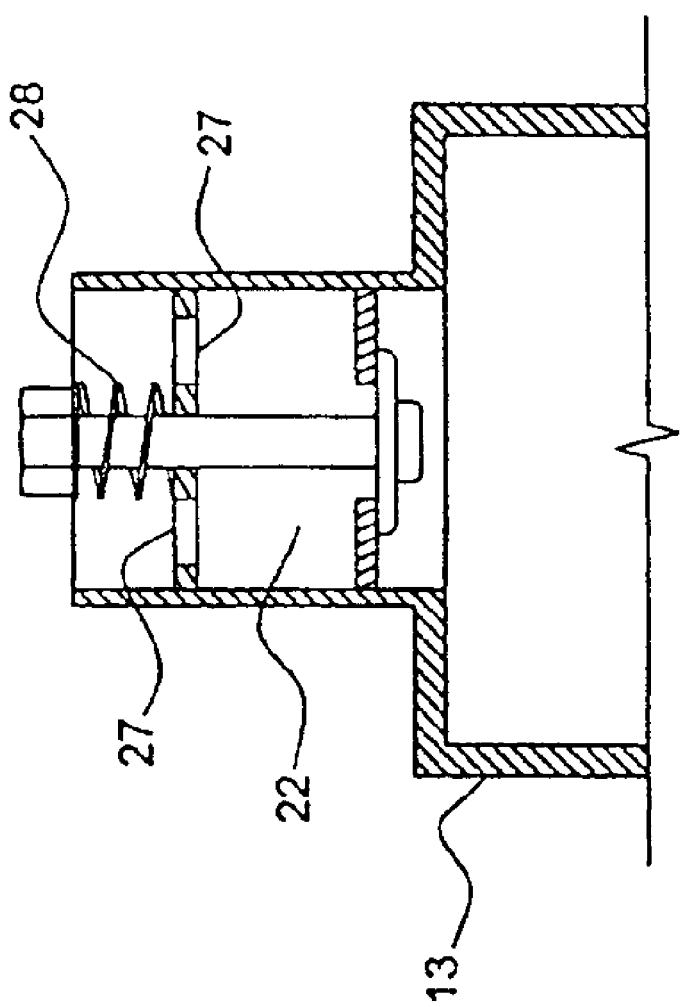
FIG. 2 is a schematic section view of a vacuum break valve for use in the apparatus of FIG. 1.

Referring to FIGS. 1 and 2, the pipestem 13 terminates at its distal end in a vacuum break valve 22 opening pipestem 13 and thus surge tank 16 to the ambient air via ports 27 when the valve 22 is open. The valve 22 is biased closed by a spring 28 or other biasing mechanism and is shown closed (seated) in FIG. 2. Preferably, the valve 22 is a conventional air check valve, such as one of the KBI-CV series of check valves manufactured by King Brothers Industries (Valencia, Calif.). In normal operation, a suction force effective at the surge tank air outlet port 20 draws air into the air bypass line 26, while the suction force effective at outlet basin 18 draws effluent liquid into the surge tank 16 from line 12. When the dental office suction apparatus openings 9 (FIG. 6) are closed and consequently suction apparatus line 12 is closed, the pressure inside the surge tank 16 drops as a result of the vacuum caused by the vacuum pump 11, and the increased pressure drop overcomes the biasing force of the spring 28, causing the vacuum break valve 22 to open, permitting replacement air to enter the surge tank 16 and both the airflow and liquid effluent flow to be maintained through the system. When the suction apparatus openings 9 are reopened, air entering into the surge tank 16 through the surge tank inlet port 14 neutralizes the pressure differential at the vacuum break valve 22, permitting the spring 28 to re-close the vacuum break valve 22. The pressure drop at which valve 22 opens can be adjusted by varying the selected compression and stiffness of the spring 28.

The level sensor port 24 shown atop surge tank 16 in FIG. 1 receives a level sensor probe 30 inserted therethrough and sealed into the sensor port 24, only the upper portion of which probe 30 appears in FIG. 1. Preferably, the probe 30 is a conventional fluid level detection sensor responsive to changes in dielectric constant between effluent fluid and air and having a plurality of sensing means, each sensing means connected to an associated wire pair among the wire pairs of a level signal cable 25, the sensing means being vertically spaced from one another within the surge tank 16. When the liquid level within surge tank 16 reaches any particular sensing means, the sensor is responsive to the change in dielectric constant between the air and the effluent fluid in the surge tank 16, and transmits a signal along the wire pair attached to the sensor. The associated wire pairs of cable 25 connect the liquid level sensors to warning display unit 32.

The display unit 32 comprises one or more audible alert devices 34 and a series of visual alert devices 35 that are responsive to the data level signals so as to provide alert or warning signals indicating the level of effluent within the surge tank 16. In a preferred embodiment, the probe 30 responds to liquid levels within the surge tank 16 at the ¼ full, ½ full, ¾ full and ⅞ full values, and at each such liquid level, the display unit 32 provides a suitable warning signal using, for example, lamps of different colours to correspond to different liquid levels. Further, when the liquid level in the surge tank 16 has reached the ⅞ level, the user is alerted by a more urgent signal (e.g. an audible signal) warning of the risk that the surge tank 16 may soon be full. The user may in response to such warning increase the flow rate out of sedimentary deposit tank 38, or reduce the incidence of use of the dental chair suction drains 9, or take other remedial measures. In an alternative embodiment, the liquid level sensor means may be mounted externally on the sides of the surge tank 16 located at appropriate levels to indicate when the tank is ¼ full, ½ full, ¾ full and ⅞ full, for example.

If effluent is deposited into the surge tank 16 when the surge tank 16 is full, excess effluent is sucked through the air outlet port 20 and is pulled by vacuum pump 11 along liquid bypass conduit 120 running in parallel with the air bypass conduit 26 and discharged from the apparatus 10 into the municipal drain (thereby preventing effluent from backing up through the pipestem 13, suction apparatus exhaust conduit 12, and eventually the suction apparatus openings 9). Preferably, no effluent is deposited into the suction apparatus openings 9 when the surge tank 16 is full, as target particles in the effluent discharged through the air bypass conduit 26 will not be separated from the effluent by sedimentary deposit tank 38. As a precaution in the event that passage of liquid effluent containing solid particles through the bypass conduit 26 does occur, pinnacle filter 89 (FIG. 1) is intended to catch at least the larger target particles that are present in such effluent, thereby tending to avoid damage to the vacuum pump 11 and to afford an "insurance" opportunity to remove unwanted particles before they pass into the municipal system. However, it is best to avoid operation of the system that results in any passage of liquid through bypass conduit 26.

Figure 3:
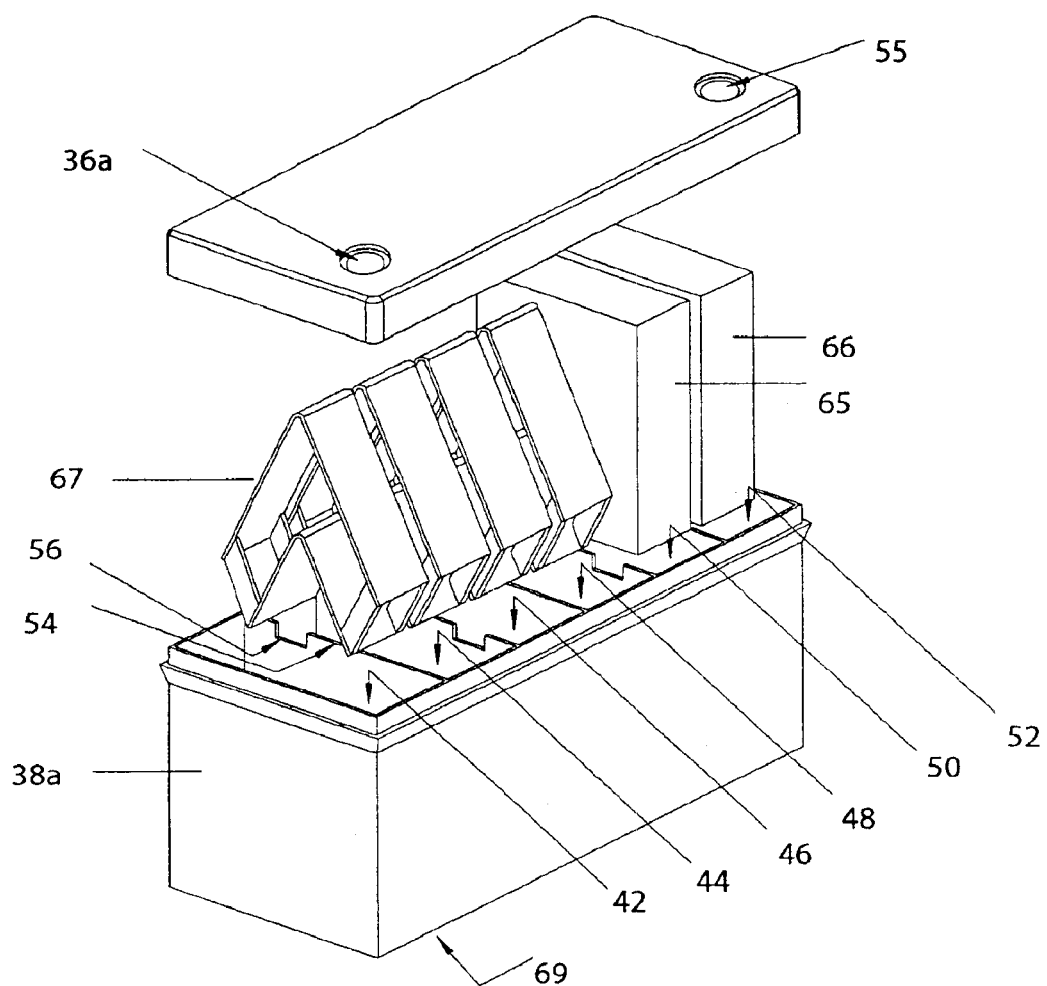
FIG. 3 is a schematic isometric view of the sedimentary deposit tank of FIG. 1 in exploded view illustrating the internal construction of the sedimentary deposit tank, including baffle chamber walls, removable baffles and sedimentary deposit tank lid.

Referring to FIGS. 1 and 3, effluent from surge tank outlet basin 18 passes through a sedimentary deposit tank inlet port/pipestem/coupling 36a and into sedimentary deposit tank 38a. The sedimentary deposit tank 38a is provided with a plurality of baffle chambers 42, 44, 46, 48, 50, 52, one or more precipitant inlet ports 53 sealed to the top of sedimentary deposit tank 38, and a deposit tank outlet conduit/pipestem 55a.

As shown in FIG. 3, the baffle chambers 42, 44, 46, 48, 50, 52 are bounded by transverse baffle chamber boundary walls 54. Each baffle chamber wall 54 is arranged vertically and parallel to the other baffle chamber walls 54. Each baffle chamber wall 54 has a wall opening 56 in the form of a rectangular notch located near the top edge of the baffle wall 54. The wall openings 56 alternate in transverse position so as to maximize the effluent travel distance from one wall opening 56 to the next. The side and bottom edges of each baffle chamber wall 54 are connected to the interior surfaces of the sedimentary deposit tank 38a to form a fluid-tight seal so that effluent can flow from one baffle chamber to an adjacent baffle chamber only through the common baffle chamber wall opening 56. In a preferred embodiment of the sedimentary deposit tank 38a the baffle chamber walls 54 are formed as integral parts of the tank unit. Alternatively, in a further embodiment of the sedimentary deposit tank 38a, the baffle chamber walls 54 may be formed separately from the tank 38a and may be removably inserted into mating slots located on the walls and bottom of the deposit tank 38a to divide the tank into separate baffle chambers.

In the preferred embodiment, the baffle chambers comprise, in downstream order: an inlet baffle chamber 42, a second baffle chamber 44, a third baffle chamber 46, a fourth baffle chamber 48, a fifth baffle chamber 50, and an outlet baffle chamber 52, although the number and size of baffle chambers is within the designer's discretion.

Figure 4:
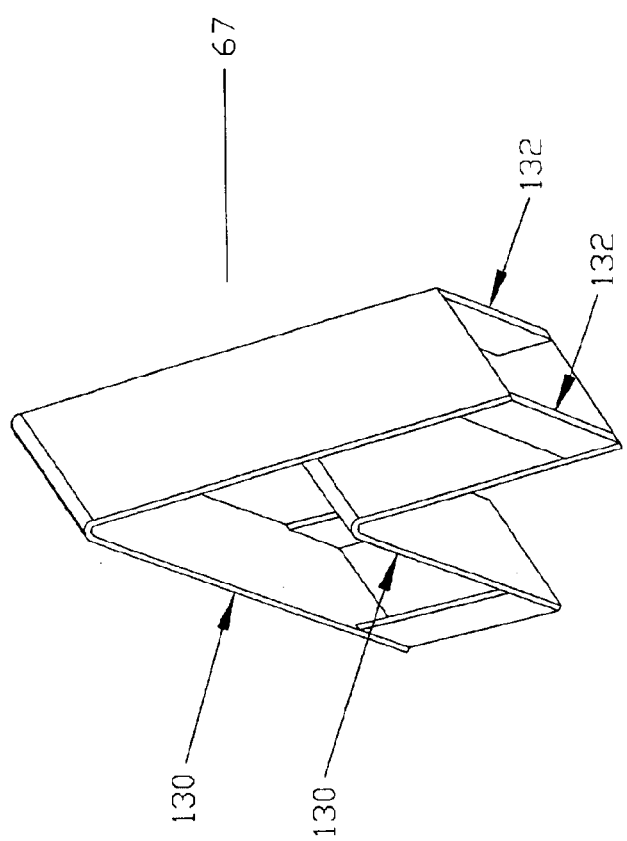
FIG. 4 is an isometric view of a multi-surface chevron-shaped baffle unit according to the invention.
Figure 5:
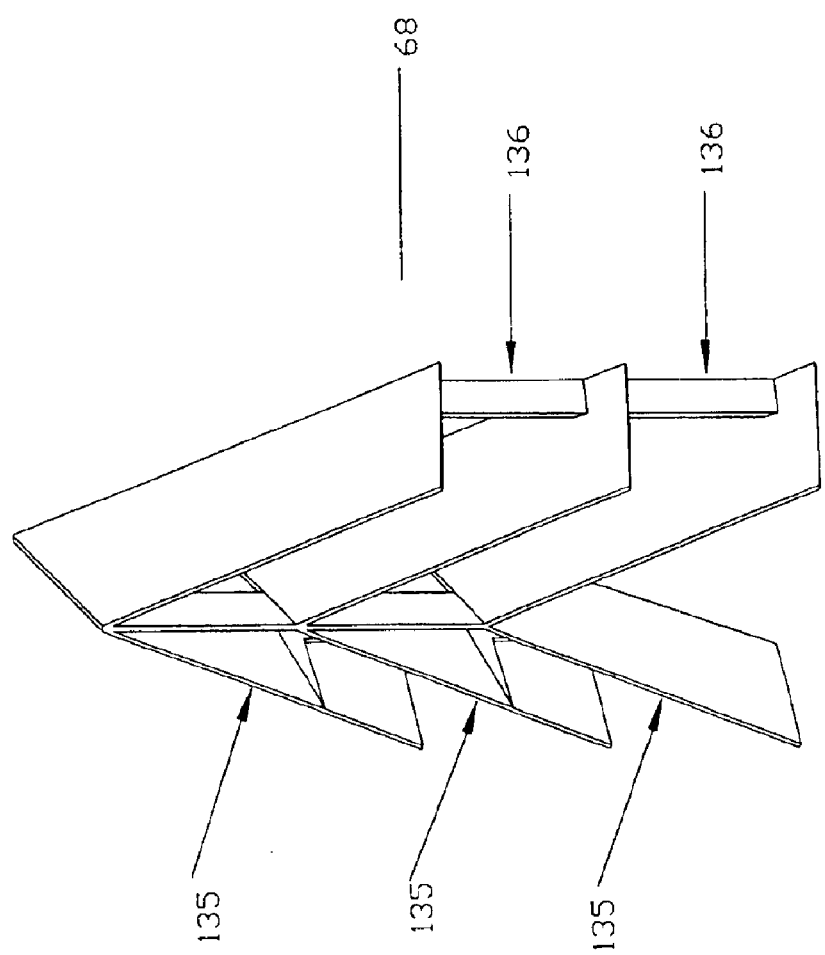
FIG. 5 is an isometric view of a multi-surface gable-shaped baffle unit according to the invention.

Referring to FIGS. 3, 4, and 5, the inlet, second, third, fourth and fifth baffle chambers 42, 44, 46, 48, 50 comprise inclined (either in one dimension or two dimensions) baffle units 67, 68 selectively arranged within each baffle chamber 42, 44, 46, 48, 50, 52 so that each baffle unit 67, 68 directs the fluid flow but does not interrupt it. In a preferred embodiment of the invention, the baffle units 67, 68 may be either chevron-shaped elements 67 as shown in FIG. 4 or gable shaped elements 68 as shown in FIG. 5, depending on the needs of the user and the characteristics of the effluent to be treated. In an alternative embodiment, the baffle surfaces may be simply inclined planar surfaces, similar to those disclosed in the applicant's previously published PCT International Patent Application No. PCT/CA99/00665 filed on 21 Jul. 1999, from which this application claims priority. Referring to FIG. 3, liquid passes from inlet baffle chamber 42 to the second baffle chamber 44 via port 56, from the second baffle chamber 44 via a second port 56 to the third baffle chamber 46, and thence to the fourth baffle chamber 48 via a third port 56. Preferably, the surfaces of the baffle units 67, 68 lie at an angle of about 60° to the deposit tank floor 69, and in the case of the gable-shaped baffle units 68 angled in two dimensions, a secondary angle of about 30° to the baffle chamber walls (54) so as to optimize convection of the effluent through the baffle chambers and particle separation. The user may wish to consult published experimental studies of preferred inclined sedimentation techniques, such as *Importance of Convection to the Enhancement of Erythrocyte Sedimentation Rates in Inclined Tubes*, Hocking et al. (Biorheology, 24; 473–482, 1987). Hocking shows that the rate of settling of erythrocyte particles from liquid whole blood onto a surface increases as the angle of the surface is increased, reaching a maximum settling rate when the surface is 60° from the horizontal plane, and that selective placement of the surfaces encourages advantageous fluid flow patterns for increased particle separation.

In a preferred embodiment of the invention designed to minimize manufacturing costs associated with producing baffles, chevron or gable-shaped baffles 130, 135 are formed individually with attached flanges or ribs 132, 136 to provide for separation of multiple baffles when stacked in a baffle chamber. In the case of chevron-shaped baffles 130, such separation ribs 132 are located near the outer edges of the baffle, and may be oriented parallel to effluent flow as illustrated in FIG. 4, or alternatively, perpendicular to effluent flow, similar to ribs 135 shown in FIG. 5. Such separation ribs 132 may also be located along the baffle centerline, and may be rectangular or cylindrical in cross section. In the case of gable-shaped baffles 135, such separation ribs 136 are located near the outside edges of the baffle, and near the central apex of the baffle, and may be oriented parallel or perpendicular to effluent flow similar to ribs 132 and 136 in FIGS. 4 and 5, or may alternately be located along the baffle centerline, and may be rectangular or cylindrical in cross section. In a further preferred embodiment designed to minimize the cost of assembling sedimentary deposit tank equipment, two or more baffles 130, 135 may be formed together as a single integrated baffle unit 67, 68 including spacing ribs 132, 136 to align and separate the baffles as discussed above. In such an embodiment, for applications where gable-shaped baffles 135 are used, three gable baffles 135 are preferably formed together in a vertically stacked configuration to form a single gable-shaped baffle unit 68. In applications where chevron-shaped baffles 130 are used, it is preferable to form two chevron baffles 130 together in a vertically stacked configuration to form a single chevron-shaped baffle unit 67. It is desirable to utilize variations in the number and separation (i.e. relative spacing) of baffles used in a baffle chamber (either as individually formed and stacked baffles or as jointly formed baffle units) in order to customize the arrangement of baffles inside the sedimentary deposit tank 38$a$, depending on the characteristics of the effluent to be treated. For example, in an application where the effluent to be treated is expected to contain a significant portion of very small particles, in addition to larger particles, it may be advantageous to utilize a greater number of baffles with smaller spacing therebetween in the downstream baffle chambers of the sedimentary deposit tank 38$a$, in order to increase the sedimentation of smaller particles after the larger particles have settled out in the upstream baffle chambers. It is expected that such variations in baffle configuration are best determined empirically, as they are dependent on factors such as effluent characteristics, which may vary significantly between applications.

Baffle chamber 42 is configured slightly differently from the other baffle chambers in order to accommodate the inlet pipestem 36$a$. Baffle chambers 44, 46 and 48 may be essentially identical, but the interior arrangement of the chambers and the respective size of the chambers is at the discretion of the designer.

Effluent passing into the sedimentary deposit tank 38$a$ through the deposit tank inlet port 36$a$ first collects in the inlet baffle chamber 42. As time elapses, metal particles and other solid particles heavier than the liquid effluent separate from the effluent and settle on the surface of a baffle unit 67 or 68 or on the sedimentary deposit tank floor 69; the more time that elapses, the greater the amount of gravity-induced particle separation. To separate solute metal particles dissolved in the liquid effluent, a chemical agent such as a precipitant, chelating agent, or flocculant may be controllably delivered via one or more inlet port(s) 53 by one or more delivery pump(s) 23 fed by one or more supply vessel(s) 70 and injecting chemical agent via supply conduit 29 sealed into port 53. Preferred chemical agents for dental office use include precipitants potassium iodide (KI) or sodium borohydrate ($NaBH_4$) mixed with sodium hydroxide (NaOH) or sodium sulfide ($Na_2S$), the latter combination however having a sulfurous odour, and the chelating agent EDTA, however any precipitant or chelating agent suitable for combining with solute mercury or silver or both, may be selected. Supplied in 1-molar concentrations, these chemical agents may be added to the effluent in the ratio of about 2 parts per 1000. Strong oxidizing or reducing agents should not be used in significant concentrations, as they may release mercury from particulate amalgams. Addition of a flocculant to a precipitant or chelating agent may promote further particle separation from the effluent; fungicides and anti-bacterial agents may also be contained in the supply vessel 70. The flocculant, if present, combines with metal particles and causes such particles to combine into larger masses, so that metal particle separation is further promoted. Suitable flocculants include aluminium sulfate and aluminium chloride. Anti-fungal agents include acridine dyes and anadine dyes.

The pump 23 may operate at a constant speed, delivering a constant flow of chemical agent into the tank 38$a$ while operating. However, the pump 23 should not operate when the dental office is idle during slack times, overnight or during weekends, etc. To this end, the pump 23 operates under the control of a liquid level sensing probe 117 located at the top of tank 38$a$, or preferably, attached to the side of the tank 38$a$, near the top thereof. The probe 117 may comprise a sensor responsive to changes in dielectric constant of the same general sort as described previously with reference to level sensing probe 30. During idle hours, liquid in the surge tank 16 will drain into the tank 38, and eventually the level in the tank 38$a$ will fall to a rest level determined by the height of the orifices 56. The sensing means of probe 117 should be positioned so that the sensing means detects the change in dielectric constant between the effluent and air and transmits a signal to a suitable control circuit just before the liquid level in tank 38$a$ reaches rest level. The pump 23 is controlled by the control circuit to operate when the sensing means reports the dielectric constant of the effluent, indicating that the liquid level in tank 38$a$ is above the rest level and the system is in operation.

Alternatively, the chemical agent delivery apparatus 70 could respond to a time clock to deliver a selected amount of chemical agent per selected time interval (with a selection of zero for idle hours). In a more complex arrangement, the delivery apparatus 70 could respond in part to the flow rate of effluent passing out of tank 38$a$ as determined by the setting of needle valve 85. The amount of chemical agent selected to be applied per time interval or per unit of effluent flow will be dependent in part on the chemical characteristics of the agent selected, and in part upon the expected concentration of particles in the effluent, and is usually best determined empirically.

Located at the fifth baffle chamber 50 and outlet baffle chamber 52 are modular filtration or adsorption inserts 65, 66 which may be adapted to include a range of physical and chemical characteristics, depending on the needs of the system user and the characteristics of the effluent to be treated. Such modular inserts are constructed to allow easy removal and replacement within the sedimentary deposit tank 38$a$ following saturation of filter or absorbent material with particulate or other waste matter. In a preferred embodiment, one of the modular units 65, 66 may be adapted to include an outlet baffle chamber filter positioned so that effluent passing through the outlet baffle chamber 52 and through the deposit tank outlet pipestem/port/coupling 55$a$ must first pass through the baffle chamber filter. The filter can be of fine mesh or fibrous mat or the like within a constraining cage. Preferably, the filter is made from polystyrene or polyethylene or another biologically inactive material so that microbes cannot utilize the filter material for nutrients. The filter tends to catch any floating solid matter as well as any coarser solid matter that has not settled out in the upstream baffle chambers. Preferably, any precipitants, flocculants or other chemical agents used should not generate an abundance of floating solid matter, because otherwise the filter could be quickly clogged. If necessary, the size of the filter and of the final two baffle chambers 50, 52 can be increased if a high proportion of floating matter is expected to be entrapped.

In a further preferred embodiment, one of the modular units 65, 66 may be adapted to include absorbent material used to adsorb dissolved mercury or other metal ions from effluent solution. A preferred adsorbent material is finely divided bentonite clay particles, combined with activated silica particles to form granular pellets, which may be enclosed in a porous and permeable membrane, similar in function and appearance to a tea bag. Concentrated chlorine solution may also be added to the effluent directly upstream of such an adsorbent modular unit through an appropriately located injector port 53. Such concentrated chlorine solution is effective to release metal ions from dissolved organic compounds to facilitate more efficient adsorption by the bentonite clay particles in the adsorbent modular unit, while the activated silica particles in the modular unit are effective to adsorb such dissolved organic compounds. In another preferred embodiment, one of the modular units 65, 66 may be adapted to include an auxiliary fine particulate filter, which is effective to remove residual fine particulate matter that has not settled out of suspension in the upstream baffle chambers 42, 44, 46, 48 of the sedimentary deposit tank 38a. A possible construction of the auxiliary filter is detailed below in the description of an alternative external embodiment of the filter.

In the alternative embodiment of the auxiliary fine particulate filter shown in FIG. 1, effluent passing out of tank outlet pipestem 55a next passes into the auxiliary filtration unit 74 located external to and downstream of the sedimentary deposit tank 38a for a final separation of fine particles. Preferably, the filter is an inorganic polymer filter for separating aqueous mercury from liquid. An example of such filter is disclosed in Pierce et al. *Chemically designed inorganically polymer filters for aqueous mercury separation,* (Journal of Dental Research v. 44, p. 404, 1997) Alternatively, the filter of filtration unit 74 can be a conventional dual gradient cartridge filter. Additionally mesh filters or porous membranes may also be employed depending upon available pressure differentials, flow-rate targets, and size of particulate desired to be removed. The outlet of filtration unit 74 is connected via outlet conduit 82 and thence via needle valve 85 to the common exit conduit 77. The filtration unit 74 is preferably attached to the deposit tank 38a using quick release connectors to enable easy replacement of the modular filtration unit 74 as required.

In a preferred embodiment of the invention that includes a fine particulate filter 74 in a modular unit 66 of the sedimentary deposit tank 38a, the outlet pipestem 55a of the tank includes protective sleeve assembly 144 to prevent clogging of the needle flow rate control valve 85 caused by floating particulate matter and froth or sludge which can accumulate around the exit port 55 of the tank. Such protective sleeve assembly comprises a downwardly depending inner needle valve intake pipe 142 over which is fitted a downwardly depending protective sleeve 144, which extends below the lower extremity of the inner intake pipe 142 by a margin of comfort to protect against the entrance of floating particulate matter or sludge into the intake pipe 142. The protective sleeve 144 is perforated by several radially spaced air holes 146 located near the top of the sedimentary deposit tank 38a such that effluent is drawn into the intake pipe 142 only when the fluid level in the tank is higher than the level of the lower end of the intake pipe 142. If the fluid level in the tank 38a drops below the level of the lower end of the intake pipe, air entering the air holes 146 in the protective sleeve 144 will be drawn out of the tank through the needle valve intake pipe 142 in place of effluent.

A disinfectant is added to the effluent at the individual operatory suction openings 9 to control bacterial growth and odours in the effluent treatment system. The addition of disinfectant additionally serves to break down organic particles in the effluent, releasing complexed forms of mercury and other metals, which can then be removed from solution in the settlement tank 38 through the use of chemical agents or adsorbent compounds. Preferred disinfectants are chlorine, bromine, or peroxide based, and utilized in a solid dissolvable brick form which is held in place at the individual suction openings 9 by a holding screen located in or near the opening 9 in the vacuum line.

It should be noted that depending on, the choice of chemical agents (precipitant, flocculant, chelating agent, disinfectant and adsorbent) selected for use in the treatment system, there exists a possibility for disadvantageous chemical interactions to occur, reducing the effectiveness of one or more of the agents in use. Such chemical interactions may also be affected by the composition of the effluent being treated in the system. Therefore, an optimum combination of chemical agents for use in treatment of a specific effluent stream may be determined by empirical means.

Note that the flow rate of effluent through tank 38a must be low enough that target particles have adequate opportunity to settle out. In a typical dental office using a vacuum pump 11, drawing a vacuum of about 25–50 kPa, a vacuum differential pressure between inlet port 14 and outlet conduit 82 of about 3–10 kPa should be sufficient to establish a suitable flow rate through tank 38a, assuming a maximum effluent volume of about 5 to 10 liters between inlet port 14 and outlet conduit 82. Flow rate may be adjusted by means of a needle valve 85 in tank outlet line 76 coupled downstream of the outlet pipestem 55a atop the tank 38a and connected to the final baffle chamber 52; a flowmeter 87 permits the operator to read the current flow rate and to adjust it as required using the needle valve 85. The flow rate should be set to an empirically estimated optimal rate equal to the total expected effluent volume during a duty cycle divided by the total available time for operating the sedimentation system per duty cycle, and multiplied by an appropriate safety factor (greater than 1.0) to guard against system backup or overflow. For example, if an average dental chair produces about 1 liter of effluent per duty cycle (working day), and there are 8 dental chairs in the office served by the apparatus 10 which operates over the 8 hour working day, a needle valve flow rate setting of about 1.2 L/hr (20 mL/min) would accommodate all 8 chairs and provide a fairly steady rate of flow through the sedimentary deposit tank 38 throughout the duty cycle, incorporating a safety factor of 1.2 to guard against system backup. These devices 85, 87 are preferably positioned in the separation system downstream of any removable modular devices such as the tank 38a and any auxiliary filter 74 present, and upstream of the junction of the tank exit conduit 79 leading from tank 38a and the common exit conduit 77.

It is desirable to utilize the minimum possible flow rate of effluent through the separation system to maximize the time for the particles to separate from the effluent. However, the flow rate may be changed if, for example, the surge tank 16 becomes backed up with effluent. The volume of effluent per dental chair per day may vary office by office and pursuant to national preferences, regulations, etc. The use of cuspidors, ultrasonic scalers and other optional dental office equipment may increase the volume of effluent produced. The optimal effluent flow rate through the sedimentary deposit tank 38a can be estimated empirically as outlined above such that the total effluent volume generated during a duty cycle passes through the system as slowly as possible without overflowing the surge tank 16. The flow rate through the apparatus 10 may be further controlled (in addition to by adjusting the needle valve 85) by adjusting the suction force of the vacuum pump 11.

There is a tendency of particles to settle out in the upstream baffle chambers rather than the downstream baffle chambers within tank 38. So the upstream chambers tend to fill up and clog the undersides of the baffles 67, 68 before the downstream chambers become very full of solid matter. A balance must be struck between maintaining optimal operation of the baffles, on the one hand, and avoiding undue frequency of cleaning or replacement of tanks 38, on the other hand. The user should choose empirically how full a tank 38a must be before it is cleaned out or replaced by a fresh empty tank. To this end, a solids level sensor 116 may be provided to indicate the level of deposited solids in, say, the third or fourth baffle chamber of the tank. Dielectric constant sensor technology similar to that commonly used in "stud sensor" units may be used for such a solids level sensor, where the sensor 116 is responsive to the change in dielectric constant between effluent liquid in tank 38a and deposited solids. When the level of solids rises to the level of the sensor, the sensor detects the change in dielectric constant, transmitting a signal to an appropriate control circuit located in display box 32 via signal cable 45. When that happens, the control circuit in display box 32 provides a warning (by warning lamp or the like) that the tank 38a is full and should be cleaned out or replaced by a fresh empty tank. While FIG. 1 shows an alternative embodiment of the invention wherein the solids level sensor 116 is mounted to the top of the sedimentary deposit tank and protrudes therein, in a preferred embodiment of the invention, such sensor 116 may be mounted on the outside of the side wall of the third or fourth baffle chamber of the tank at a threshold level selected by the user.

Periodically, it is desirable to remove the metal particles collected in the sedimentary deposit tank 38a and filtration unit 74. According to the preferred embodiment, the sedimentary deposit tank 38a and associated integrally constructed auxiliary modular filtration units 65, 66 are removably connected to the apparatus 10 as readily coupled/ decoupled modular units. To this end, all conduit or port couplings and all electrical connections should be of the quick-release type. The tank 38a and other modular units can be removed from the apparatus 10 for metal particle recovery and cleaning, for example, at a metal particle recovery facility.

The air bypass vacuum line 26 is coupled to the surge tank 16 via a bypass coupling collar 88 that is adapted to removably connect the vacuum line to the air outlet port 20, and the base of pipestem 13 also preferably includes a release coupling so that the surge tank 16 may be decoupled for cleaning.

Bypass conduit 84 including shut-off valve 86 connects the surge tank pipestem 13 to the air bypass line 26. The bypass valve 86 is normally closed when the surge tank 16 and sedimentary deposit tank 38a are connected to the apparatus 10, but is opened when the tank 38a is removed. When the sedimentary deposit tank 38a is removed, valve 100 leading from exit basin 18 is closed. Eventually the surge tank 16 may become full of effluent. Air then passes through the suction apparatus exhaust conduit 12, through the upper portion of pipestem 13, through the by-pass conduit 84, and into the air bypass conduit 26, for discharge into the vacuum draw line 77 and thence into the municipal drain. When eventually liquid effluent passes from a full surge tank 16 out of outlet port 20, the liquid passes through liquid bypass conduit 120 running in parallel with the air bypass conduit 26, and eventually joins common exit conduit 77 upstream of pinnacle filter 89. This temporary vacuum circuit enables the dental office suction apparatus to keep functioning, albeit without as much solids removal as would occur if tank 38a were connected, but with some solids removal by means of pinnacle filter 89.

Figure 7:
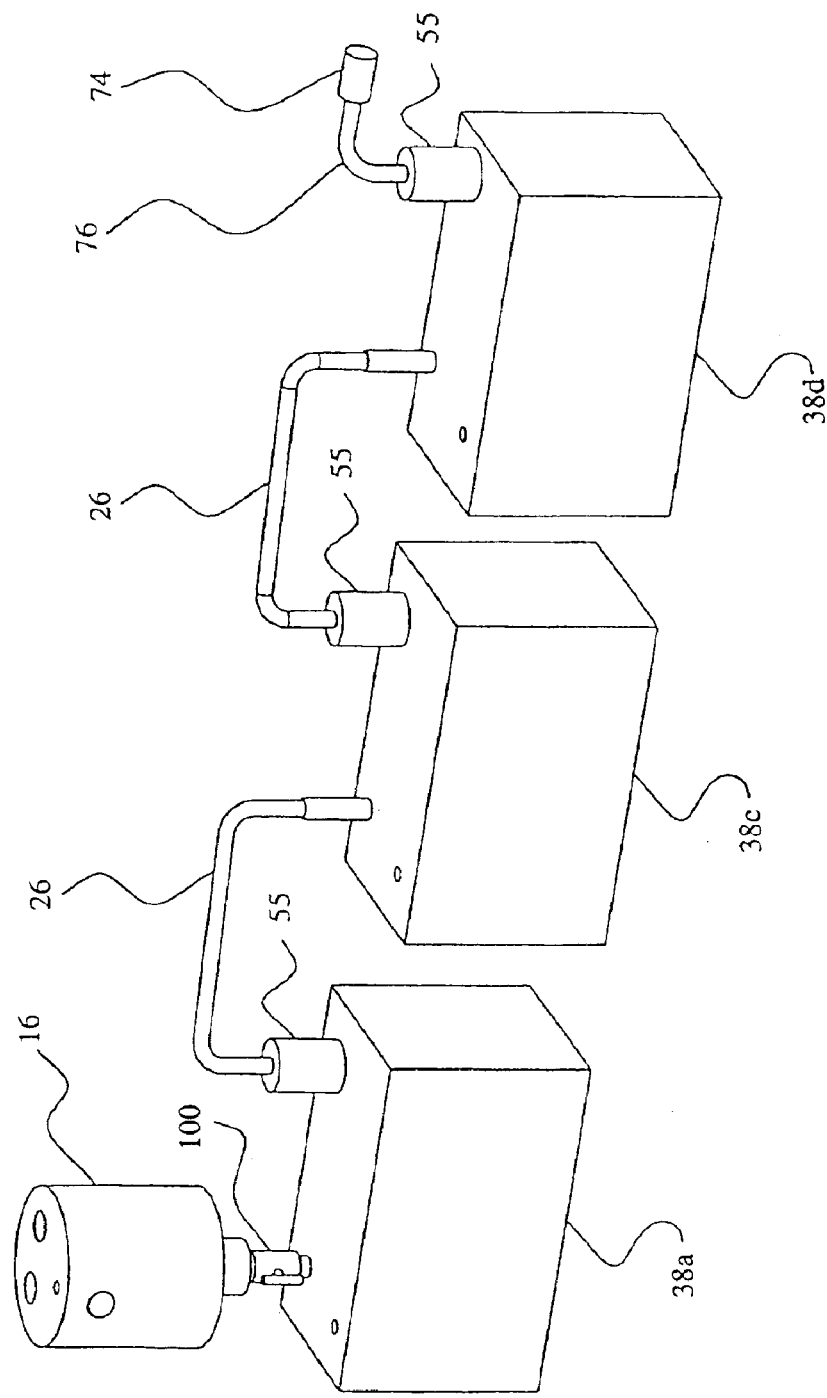
FIG. 7 is a schematic isometric view of a portion of a preferred embodiment of particle removal apparatus according to the invention, showing the surge tank and an exemplary three sedimentary deposit tanks coupled together in series.
Figure 8:
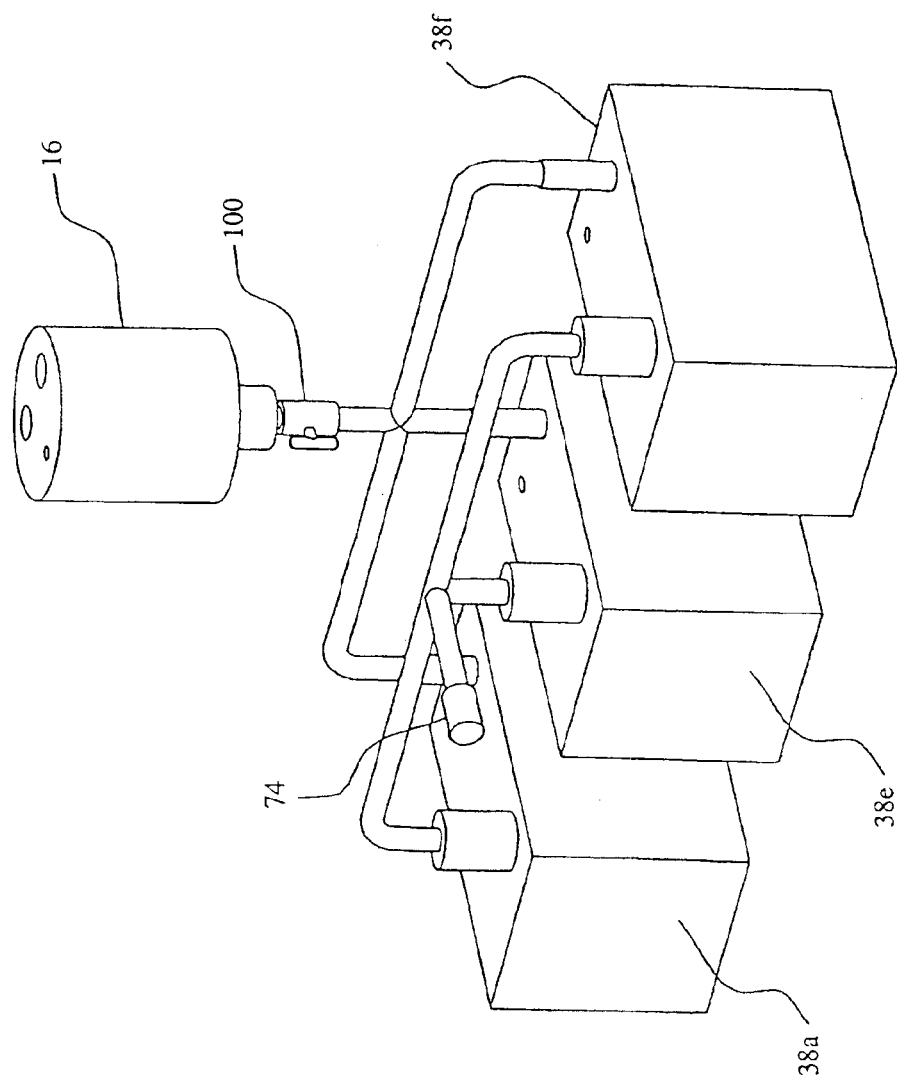
FIG. 8 is a schematic isometric view of a portion of a preferred embodiment of particle removal apparatus according to the invention, showing the surge tank and an exemplary three sedimentary deposit tanks coupled together in parallel.

To avoid temporary problems associated with removal and replacement or cleaning of sedimentary deposit tank 38, it is desirable to use two or more modular sedimentary deposit tanks operating in parallel or series. FIG. 7 illustrates an exemplary series connection of three sedimentary deposit tanks 38a, 38c, 38d, and FIG. 8 illustrates an exemplary parallel connection of three sedimentary deposit tanks 38a, 38e, 38f. Each such sedimentary deposit tank would be provided with its own solids level indicator so that each upon being considered "full" would be removed and replaced. The use of two or more sedimentary deposit tanks in series extends the flow distance for the effluent to pass through the apparatus 10 compared to that for a single sedimentary deposit tank. Therefore, greater separation of particles may be achieved for a given flow rate, or a higher flow rate may be applied through the apparatus 10.

Figure 9:
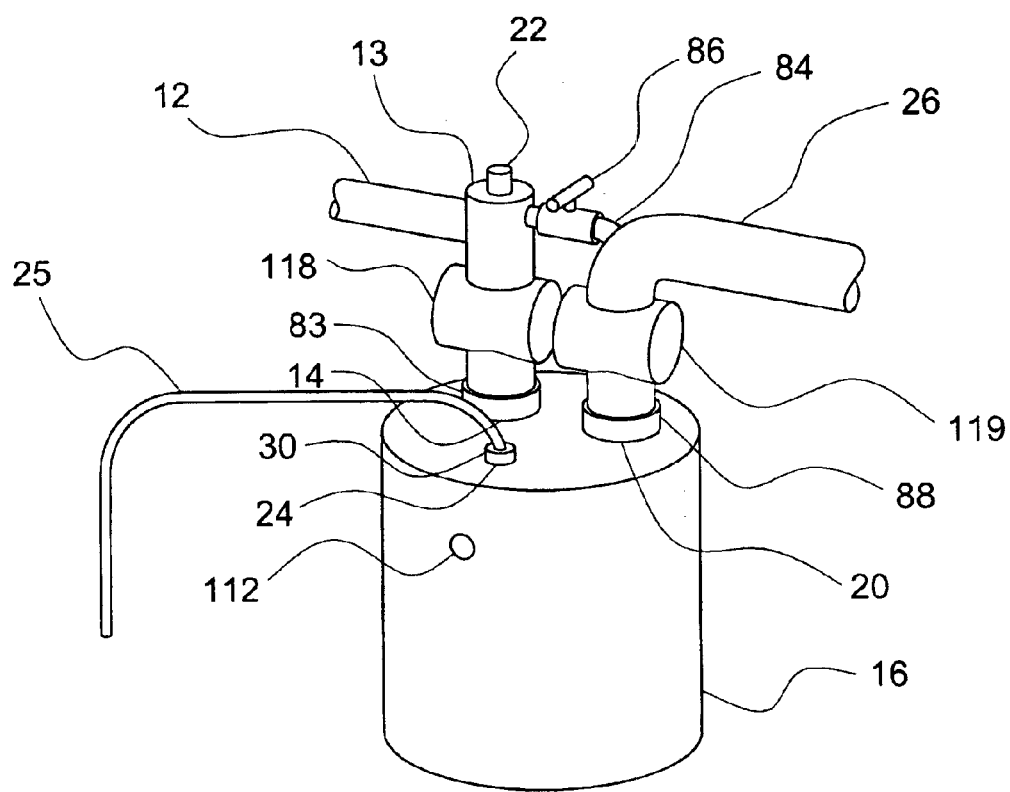
FIG. 9 is a schematic isometric view of an alternative preferred embodiment of a surge tank according to the invention, for use with a positive air pressure system.
Figure 10:
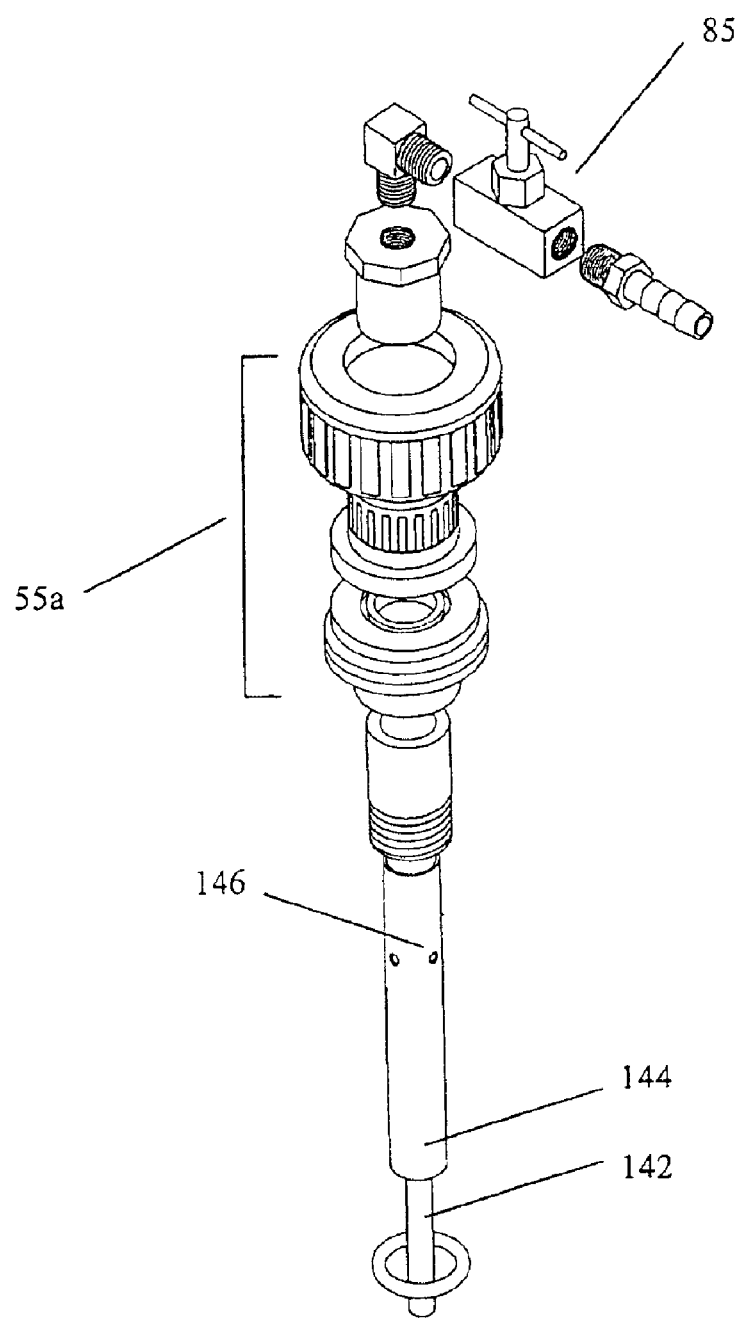
FIG. 10 is an isometric view of a preferred embodiment of an outlet pipe structure for a sedimentary deposit tank, illustrating an anti-sludge protecting sleeve and needle valve.

If a positive air pressure source instead of a vacuum source is connected to provide the requisite pressure differential between the inlet port of the surge tank 16 and the exit conduit 77, or if the vacuum pump 11 may be operating only intermittently, a modified version of the plumbing atop the surge tank 16 as shown in FIG. 9 is appropriate. (In Europe, it is common for the vacuum pump 11 to turn off when not in active use; in North America, the vacuum pump 11 tends to run constantly, at least during office hours.) Valves 118 and 119, interposed between the surge tank 16 and conduits 12 and 26 respectively, are normally open when the dental office drains are operating, in which case the positive upstream air pressure in line 12 drives effluent downstream through the surge tank 16 and sedimentary deposit tank 38, and drives air downstream through air bypass conduit 26. When the dental office drains are not operating, in which case no upstream air pressure is applied, both valves 118, 119 close. In such latter instance, an air inlet port 112 located in the upper part of the surge tank 16 opens, applying a modest air pressure to the interior of the surge tank 16 to compensate for the lack of air pressure in conduit 12. Valve 118 can be a check valve that, like valve 22, operates in response to pressure changes. Valve 119 and the air pressure supply to air inlet port 112 may be solenoid actuated in response to interruption in the supply of air pressure to conduit 12. The supply of air to air inlet port 112 is also preferably responsive to liquid level sensor probe 117 or the equivalent, so that positive air pressure is no longer applied once the liquid level in tank 38a has dropped below the threshold level determined by the probe 117 or the like.

In some working environments, the apparatus described above whose primary use is for solids removal may be provided with auxiliary conduits for removing excess effluent from a full sedimentary deposit tank that has been replaced, and drying the tank. Such full tank contains mostly liquid and some solid. Assuming that the full tank is to be taken off premises for solids removal and waste recovery and cleaning, the tank is more easily handled if it is not full of liquid but is relatively dry. To this end, an attachment conduit 125 fitted with a valve 126 is connected to the inlet port of the surge tank 16 and is also connected to the outlet port 55b of the full sedimentary deposit tank to be dried. By tilting the full tank, and opening the valve on the attachment conduit, the excess liquid effluent can be removed from the full tank under suction, returning the effluent to the surge tank 16 and flow therefrom for retreatment in the newly installed empty sedimentary deposit tank. Following removal of excess liquid effluent from the full tank, auxiliary tank drying conduits 92, 93 may each be coupled at one end to bypass conduit 26 and at the other end respectively coupled to pipestem couplings 36b, 55b respectively of a tank 38b to be dried, as illustrated in FIG. 1. A shut-off valve 114 is interposed in line 26 between the points of connection of conduits 92, 93 with the line 26. Shut-off valves 115, 113 respectively are provided for the conduits 92, 93. When tank 38b is to be dried, valves 115, 113 are open and valve 114 is closed, forcing the air entering line 26 to pass through conduits 92, 93 and therefore the interior of tank 38b, thereby permitting the flowing air to remove water vapour from the tank 38b. When the dried tank 38b is to be removed and another tank put in its place, or whenever the drying option is not to be used, valves 115, 113 are closed and valve 114 is open, directing the air along conduit 26 without passing through conduits 92, 93.

As the air entering the conduit 26 is invariably humid, the drying option described above 4 may not work well in all situations. A heater (not shown) could be provided to warm the air before it enters tank 38b, but that increases the expense of manufacture and the operating expense. An auxiliary tank drying apparatus separate from the effluent treatment apparatus would be more economical in some situations.

Mercury vapour may remain in the air line; it will not be entrapped by the sedimentary deposit tank 38a nor by filters downstream thereof because the vapour preferentially passes through bypass conduit 26. A mercury vapour trap or filter 101 may be provided in the conduit 26 to remove at least some mercury from the effluent air. A suitable mercury vapour filter is described in Boliden U.S. Pat. No. 5,205,743 issued 27 Apr. 1993; selenium is a suitable material for use in such filters. Activated charcoal impregnated with various active mercury bonding agents may also be used. Note that the mercury vapour trap will also catch such vapour emanating from the tank 38b being dried.

Note that the provision of liquid effluent bypass conduit 120 located beneath air bypass conduit 26 permits excess liquid to flow from surge tank 16 to common exit conduit 77 without interfering with air flow through the drying conduits 92, 93 and without interfering with the operation of the mercury vapour filter 101. The bypass line 120 should join conduit 77 upstream of pinnacle filter 89 so as to remove at least coarser solids in the event of such overflow from surge tank 16.

An alterative embodiment of the present invention is oriented towards institutional or other large-scale use where many dental chairs or other sources of effluent are connected to the same suction and effluent discharge services, such that the volume of effluent generated during a duty cycle exceeds the capacity of a single settlement tank 38. In one such large scale installation, the effluent travels through two or more settlement systems arranged in parallel, each settlement system composed of a surge tank 16 connected to preferably one, but alternatively two settlement tanks 38. The common main vacuum line 12 connects to two or more surge tanks 16a, 16b through one or more T-junction connectors. Similarly, the treated effluent exiting the settlement tanks 38 through the tank exit conduits 79 are connected to a common main exit conduit 77. The pressure differential required to move the effluent through the parallel settlement systems can be provided by the common system vacuum pump 11 as in the small dental office installation described above, or by a separate auxiliary effluent pump 160.

The use of a separate effluent pump 160 allows the settlement system to operate 24 hours per day, independent of the operation of the system vacuum pump 11. This allows the reduction of the minimum possible effluent flow rate by lengthening the settlement time to process effluent from one duty cycle, optimizing sedimentation. Therefore, the optimum effluent flow rate becomes the total volume of effluent generated in one duty cycle (an 8 hour working day) divided by the total available time for operation of the system per duty cycle (24 hours due to continuous operation of effluent pump 160), multiplied by an appropriate safety factor to guard against system backup. Additionally, a separate effluent pump 160 also eliminates the need to individually calibrate vacuum needle valves 85 on each settlement tank 38 in order to ensure equal effluent flow through each tank 38 installed in parallel, instead, in an installation where a separate effluent pump 160 is utilized, the main system vacuum pump 11 is connected only to the surge tanks 16, but not also to the individual settlement tanks 38 as in the small dental office installation. In addition, when a separate effluent pump 160 is used, the treated effluent leaving the settlement tanks through tank exit conduits 79 flow into a common effluent drain 162 which is separate from the main vacuum exit conduit 77.

Figure 11:
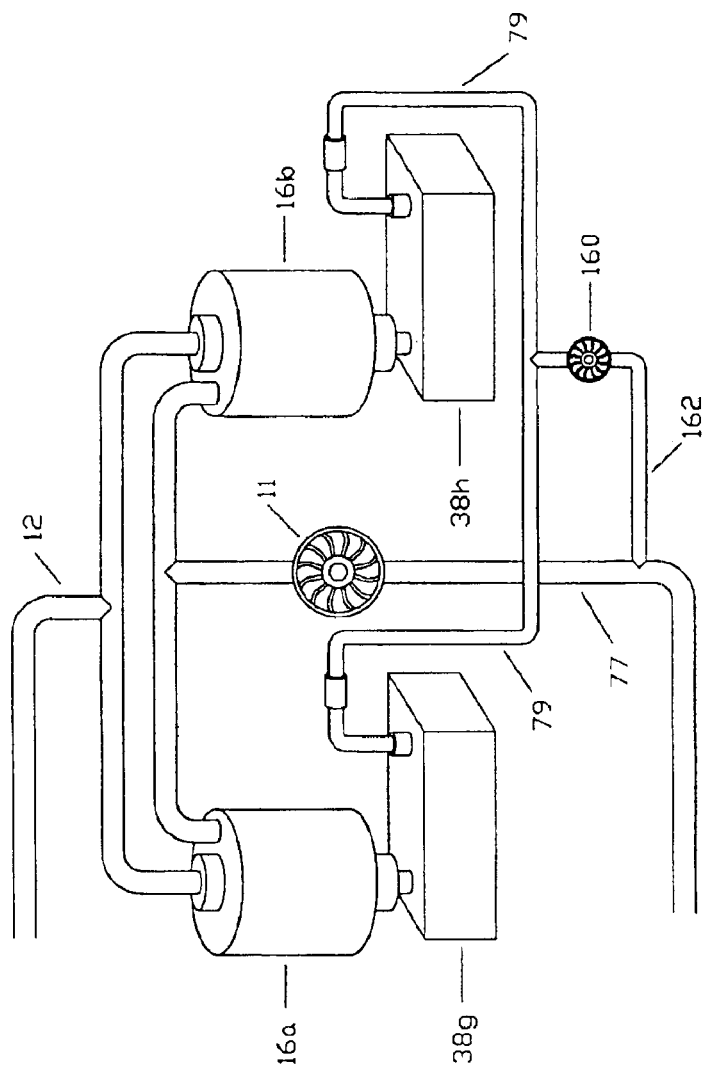
FIG. 11 is an isometric view of a preferred embodiment of a large scale institutional application of the present invention, illustrating one separate auxiliary effluent pump located downstream of multiple sedimentary deposit tanks.
Figure 12:
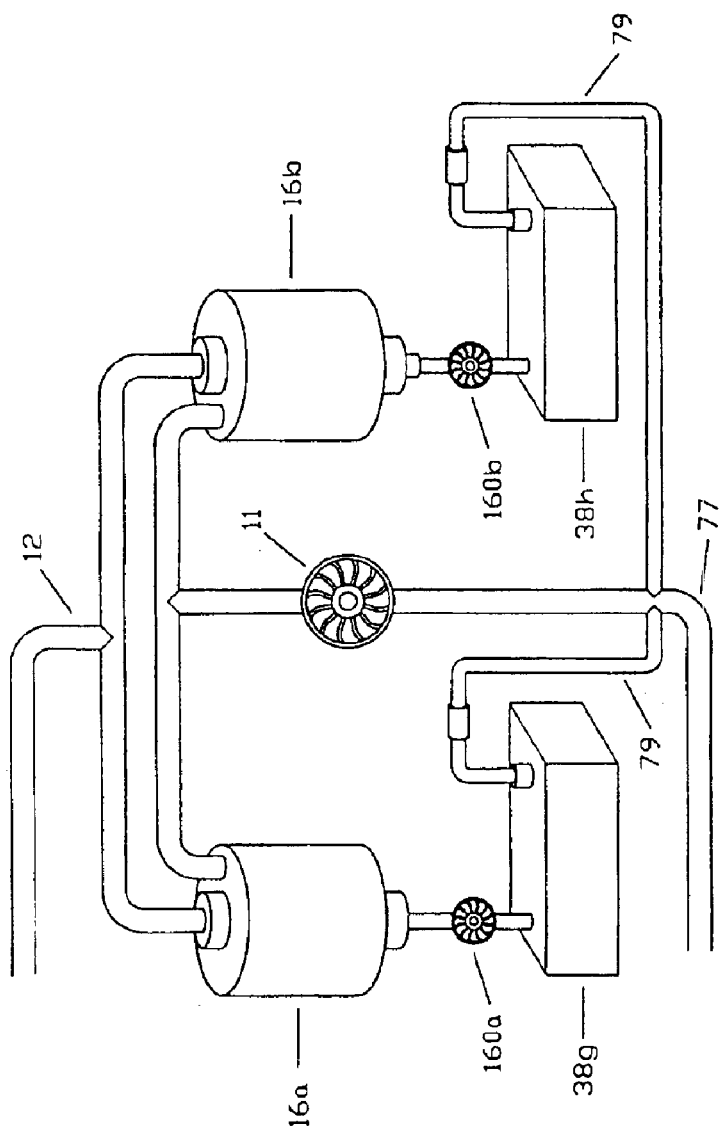
FIG. 12 is an isometric view of an alternative embodiment of a large scale institutional application of the present invention, illustrating multiple separate auxiliary effluent pumps located upstream of the multiple sedimentary deposit tanks.

As shown in the preferred embodiment of a large institutional installation in FIG. 11, the separate effluent pump 160 is preferably located downstream of the settlement tanks 38g, 38h in order to reduce wear on the pump caused by abrasion from amalgam and other particles suspended in the effluent before sedimentation, and to reduce the dissolution of mercury into the effluent caused by the turbulence inside the effluent pump 160. In an alternative embodiment shown in FIG. 12, multiple separate effluent pumps 160a, 160b can be located upstream of the settlement tanks 38g, 38h between the individual surge tanks 16a, 16b and the settlement tanks 38g, 38h to force effluent through the tanks by positive pressure. The schematic representations of the large institutional installations shown in FIGS. 11 and 12 omit many of the detailed elements of the treatment system for the sake of clarity, however, it is expected that the additional system elements as shown in FIGS. 1, 2 and 9 and described in the foregoing will remain part of such institutional installations including such elements as fluid and solid level sensors and control systems, conduits and flow control valves, chemical agent injection ports and supply pumps, pinnacle filters, auxiliary effluent suction conduits, and the like.

Other alternatives and variants of the above described methods and apparatus suitable for practising the methods will occur to those skilled in the technology. The scope of the invention is as defined in the following claims.

What is claimed is:

1. A system for separating particles from a particle-laden liquid effluent drawn from a suctioning device, comprising;
    (a) a surge tank for receiving said effluent, said surge tank having a surge tank inlet in fluid communication with said auctioning device, a surge tank liquid effluent outlet and a surge tank air outlet;
    (b) a sedimentary deposit tank, said sedimentary deposit tank acting primarily under the influence of gravity to cause settlement of said particles, and having a sedimentary deposit tank inlet connected to said surge tank liquid effluent outlet;
    (c) a vacuum pump having a vacuum pump inlet;
    (d) a by-pass conduit establishing fluid communication between said surge tank air outlet and said vacuum pump inlet and said sedimentary deposit tank outlet being connected to said by-pass conduit such that when said vacuum pump is operating, the vacuum pump arts to draw said liquid effluent from said surge tank through said sedimentary deposit tank and said by-pass conduit and to draw air from said surge tank air outlet through said by-pass conduit.

2. A system as in claim 1 wherein when said vacuum pump is operating, the pressure at the suctioning device is higher than the pressure inside the surge tank and the pressure inside the surge tank is higher than the pressure at the vacuum pump inlet.

3. A system as in claim 2 wherein said suctioning device is a dental operatory suctioning device.

4. A system as defined in claim 3, further comprising a flow inhibiting means for inhibiting the flow of liquid effluent through the sedimentary deposit tank for facilitating the settling of particles within the sedimentary deposit tank.

5. A system as defined in claim 4, wherein the flow inhibiting means comprises a constriction of the liquid effluent flow path in the vicinity of the sedimentary deposit tank outlet.

6. A system as defined in claim 5, wherein the constriction comprises a conduit connected between the sedimentary deposit tank outlet and the air bypass conduit, sized so as to constrict the flow of liquid effluent.

7. A system as defined in claim 4, wherein the flow inhibiting means comprises a constriction of the liquid effluent flow path in the vicinity of the sedimentary deposit tank inlet.

8. A system as defined in claim 7, wherein the constriction comprises a conduit between the surge tank effluent outlet and the sedimentary deposit tank inlet sized so as to constrict the flow of liquid effluent.

9. A system as defined in claim 4, wherein the flow inhibiting means is a flow controlling means.

10. A system as defined in claim 9, wherein the flow controlling means is a throttle valve in the vicinity of the sedimentary deposit tank outlet, whereby the flow rate of effluent may be adjusted by adjusting the throttle valve.

11. A system as defined in claim 10, wherein the throttle valve is a needle valve.

12. A system as defined in claim 11 wherein the cross sectional area of the liquid effluent flow path in the vicinity of the sedimentary deposit tank outlet is less than the cross-sectional area of the liquid effluent flow path in the vicinity of the sedimentary deposit tank inlet, so as to reduce the flow rate of liquid effluent out of the sedimentary deposit tank via the sedimentary deposit tank outlet as compared to the potential flow rate of liquid effluent into the sedimentary deposit tank via the sedimentary deposit tank inlet.

13. A system as defined in claim 3, wherein the sedimentary deposit tank is detachably coupled to the surge tank effluent outlet and the air bypass conduit, wherein the sedimentary deposit tank is readily detachable for emptying and replacement.

14. A system as defined in claim 3, further comprising one or more filters through which liquid effluent passes en route to the vacuum pump.

* * * * *

UNITED STATES PATENT AND TRADEMARK OFFICE
CERTIFICATE OF CORRECTION

PATENT NO. : 6,946,069 B2
DATED : September 20, 2005
INVENTOR(S) : Chilibeck

It is certified that error appears in the above-identified patent and that said Letters Patent is hereby corrected as shown below:

<u>Title page,</u>
Item [56], References Cited, U.S. PATENT DOCUMENTS, "...Rozkydaiek" should be -- ...Rozkydalek --.

<u>Column 1,</u>
Line 10, "...now U.S. Pat. No. 6,596,754..." should be -- ...now U.S. Pat. No. 6,592,754... --.

<u>Column 18,</u>
Line 6, "...that depending on, the choice of..." should be -- ...that depending on the choice of... --.

<u>Column 22,</u>
Line 11, "...installed in parallel, instead, in an..." should be -- ...installed in parallel. Instead, in an... --.
Line 52, "...said auctioning device,..." should be -- ...said suctioning device,... --.
Line 64, "...the vacuum pump arts to draw said..." should be -- ...the vacuum pump acts to draw said... --.

Signed and Sealed this

Fourth Day of April, 2006

JON W. DUDAS
*Director of the United States Patent and Trademark Office*